US007521220B2

(12) United States Patent
Pau et al.

(10) Patent No.: US 7,521,220 B2
(45) Date of Patent: *Apr. 21, 2009

(54) PRODUCTION OF VACCINES

(75) Inventors: Maria G. Pau, Leiden (NL); Alphonsus G. C. M. UytdeHaag, Vleuten (NL); Govert J. Schouten, Leiderdorp (NL)

(73) Assignee: Crucell Holland B.V., Leiden (NL)

( * ) Notice: Subject to any disclaimer, the term of this patent is extended or adjusted under 35 U.S.C. 154(b) by 294 days.

This patent is subject to a terminal disclaimer.

(21) Appl. No.: 11/256,352

(22) Filed: Oct. 21, 2005

(65) Prior Publication Data

US 2006/0063261 A1    Mar. 23, 2006

Related U.S. Application Data

(63) Continuation-in-part of application No. 09/722,867, filed on Nov. 27, 2000, now abandoned.

(51) Int. Cl.
  *C12N 7/00* (2006.01)
(52) U.S. Cl. .................................................. 435/235.1
(58) Field of Classification Search ................ 435/235.1
  See application file for complete search history.

(56) References Cited

U.S. PATENT DOCUMENTS

| | | | |
|---|---|---|---|
| 4,703,008 A | 10/1987 | Lin | |
| 4,835,260 A | 5/1989 | Shoemaker | |
| 5,047,335 A | 9/1991 | Paulson et al. | |
| 5,441,868 A | 8/1995 | Lin | |
| 5,457,089 A | 10/1995 | Fibi et al. | |
| 5,494,790 A | 2/1996 | Sasaki et al. | |
| 5,631,158 A | 5/1997 | Dorai et al. | |
| 5,767,078 A | 6/1998 | Johnson et al. | |
| 5,773,569 A | 6/1998 | Wrighton et al. | |
| 5,789,247 A | 8/1998 | Ballay et al. | |
| 5,830,851 A | 11/1998 | Wrighton et al. | |
| 5,835,382 A | 11/1998 | Wilson et al. | |
| 5,856,298 A | 1/1999 | Strickland | |
| 5,994,128 A | 11/1999 | Fallaux et al. | |
| 6,033,908 A | 3/2000 | Bout et al. | |
| 6,475,753 B1 | 11/2002 | Ruben et al. | |
| 6,492,169 B1 | 12/2002 | Vogels et al. | |
| 6,558,948 B1 | 5/2003 | Kochanek et al. | |
| 6,653,101 B1 | 11/2003 | Cockett et al. | |
| 6,855,544 B1 | 2/2005 | Hateboer et al. | |
| 6,878,549 B1 | 4/2005 | Vogels et al. | |
| 7,192,759 B1 * | 3/2007 | Pau et al. .................. | 435/235.1 |
| 2002/0116723 A1 | 8/2002 | Grigliatti et al. | |
| 2003/0087437 A1 | 5/2003 | Asada et al. | |
| 2003/0092160 A1 | 5/2003 | Bout et al. | |

FOREIGN PATENT DOCUMENTS

| | | |
|---|---|---|
| EP | 0 411 678 | 2/1991 |
| EP | 0 185 573 | 6/1995 |
| EP | 0 833 934 B1 | 4/1998 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 00/61164 | 10/2000 |
| WO | WO 00/63403 | 10/2000 |
| WO | WO 01/38362 A2 | 5/2001 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |

OTHER PUBLICATIONS

Donatelli, et al., 2001 J Gen Virol 2001 vol. 82, pp. 623-630.*
Pau, et al., The human cell line PER.C6 provides a new manufacturing system for the production of influenza vaccines, Vaccine 2001 vol. 19, Issues 17-19, pp. 2716-2721.*
Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.
Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1888, pp. 2718-2727, vol. 62, No. 8.
Berg et al., High-Level Expression of Secreted Proteins from Cells Adapted to Serum-Free Suspension Culture, Research Report, 1993, pp. 972-978, vol. 14, No. 6.

(Continued)

*Primary Examiner*—Bruce Campell
*Assistant Examiner*—Myron G Hill
(74) *Attorney, Agent, or Firm*—TraskBritt

(57) ABSTRACT

Means and methods for producing mammalian viruses, the method comprising infecting a culture of immortalized human cells with a virus, incubating the culture infected with virus to propagate the virus under conditions that permit growth of the virus, and to form a virus-containing medium, and removing the virus-containing medium. The viruses can be harvested and be used for the production of vaccines. Advantages include that human cells of the present invention can be cultured under defined serum-free conditions and the cells show improved capability for propagating virus. Methods are provided for producing, in cultured human cells, influenza virus and vaccines derived thereof. This method eliminates the necessity of using whole chicken embryos for the production of Influenza vaccines. The method also provides for the continuous or batch-wise removal of culture media. As such, the present invention allows the large-scale continuous production of viruses to a high titer.

14 Claims, 28 Drawing Sheets

OTHER PUBLICATIONS

Brown et al., "Evaluation of Cell Line 293 for Virus isolation in Routine Viral Diagnosis," Journal of Clinical Microbiology, Apr. 1986, pp. 704-708, vol. 23, No. 4.
Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.
Caravokyri et al., "Constitutive Episomal Expression of Polypeptide IX (pIX) in a 293-Based Cell Line Complements that Deficiency of PIX Mutant Adenovirus Type 5," Journal of Virology, Nov. 1995, pp. 6627-6633, vol. 69, No. 11.
Certificate of deposit of the PER.C6 cell line (ECACC deposit under No. 96022940), 1999
Ciccarone et al., "Lipofectamine 2000 Reagent for Transfection of Eukaryotic Cells," Focus, 1999, pp. 54-55, vol. 21, No. 2.
Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.
DuBridge et al., "Analysis of Mutation in Human Cells by Using an Epstein-Barr Virus Shuttle System," Molecular and Cellular Biology, Jan. 1987, pp. 397-387, vol. 7, No. 1.
Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.
Gallimore et al., Transformation of Human Embryo Retinoblasts with Simian Virus 40, Adenovirus and ras Oncogenes, Anticancer Research, 1986, pp. 499-508, vol. 6.
Garnier et al., Scale-up of the adenovirus expression system for the production of recombinant protein in human 293S cells, Cytotechnology, 1994, pp. 145-155, vol. 15.
GenBank Accession No. X02996.1, 1993, "Adenovirus type 5 left 32% of the genome".
Graham et al., "Characteristics of a Human Cell Line Transformed by DNA from Human Adenovirus Type 5," J. Gen. Virol., 1997, pp. 59-72, vol. 36.
Graham et al., "Growth of 293 cells in suspension culture," J. Gen Virol, Mar. 1987, pp. 937-940, vol. 68.
Graham, Cell Lines, Promochem (visited Apr. 10, 2005) <http://www.lgcpromochem-atcc.com/searchCatalogs/longview.cfm?view=ce,1146678...>.
Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.
Inoue et al., Production of Recombinant Human Monoclonal Antibody Using ras-Amplified BHK-21 Cells in a Protein free Medium, Biosci. Biotech. Biochem., 1996, pp. 811-817, vol. 60, No. 5.
Interlocutory Decision of the Opposition Division of Jul. 21, 2003 in the case EP 0 695 351(European applicaiton 94 913 174.2)/
Lopez et al., Efficient production of biologically active human recombinant proteins in human lymphoblastoid cells form integrative and episomal expression vectors, Gene, 1994, pp. 285-291, vol. 148.
Lutz et al., "The Product of the Adenovirus Intermediate Gene IX Is a Transcriptional Activator," Journal of Virology, Jul. 1997, pp. 5102-5109, vol. 71, No. 7.
Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.
Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.
Neumann et al., "Generation of influenza A viruses entirely from cloned cDNAs," Proc. Natl. Acad. Sci., Aug. 1999, pp. 9345-9350, vol. 96.
Opposition against European patent 1 108 878 B1 filed Oct. 5, 2005 in the name and on behalf of CEVEC Pharmaceuticals GmbH.
Opposition against European patent 1 161 548 B1 filed Nov. 16, 2005, in the name and on behalf of CEVEC Pharmaceutical GmbH.
Opposition against European patent 1108787 filed Oct. 5, 2005 in the name and on behalf of Probiogen AG.
Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.
Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.
Pleschka et al., "A Plasmid-Based Reverse Genetics System for Influenza A Virus," Journal of Virology, Jun. 1996, pp. 4188-4192, vol. 70, No. 6.
PubMed listing of abstracts (visited Apr. 10, 2005) <http://www.ncbi.nlm.nih.gov/.entrez/query.fcgi?CMD=search&DB=pubmed.
RHIM et al., "Development of Human Cell Lines from Multiple Organs," Annals of the New York Academy of Sciences, 2000, pp. 16-25, vol. 919.
Spector et al., "Regulation of Integrated Adenovirus Sequences During Adenovirus Infection of Transformed Cells," Journal of Virology, Dec. 1980, pp. 860-871, vol. 36, No. 3.
Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.
U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.
190 Yan et al., Novel Asn-linked oligosaccharides terminating in GalNAcbeta(1-4)[Fucalpha(1-3)]GlcNAcbeta(1- ) are present in recombinant human Protein C expressed in human kidney 293 cells, Glycobiology, 1993, pp. 597-608, vol. 3. No. 6.
Yeager et al., Constructing immortalized human cell lines, Current Opinion Biotechnology, 1999, pp. 465-469, vol. 10.
Yeh et al., Adenoviral Vectors, pp. 25-42 of "Concepts in Gene Therapy," Publisher: Walter de Gruyter, New York.
Summons to attend Oral Proceedings by the EPO for Patent No. 1108787, dated Mar. 7, 2007.
Letter from von Kreisler Selting Werner dated Dec. 21, 2007 in opposition against EP 1108787/00204190.3-2405.
Letter from Dehmel & Bettenhausen (on behalf of Cevec Pharmaceuticals GmbH) dated Dec. 21, 2007 in opposition against EP 1108787 B1 (00 204 190.3) with enclosure.
Patience et al., Infection of human cells by an endogenous retrovirus of pigs, Nature Medicine, vol. 3, 1997, pp. 282-286.
Davis et al., Microbiology, Lippincott Company, Fourth Edition, 1990, p. 770.
Letter from Vossius & Partner dated Dec. 21, 2007 in opposition against EP 00204190.3/1108787 with enclosures.
Declaration of Dr. Uytdehaag signed Dec. 20, 2007 with attachments.
Hoffmann et al., A DNA transfection system for generation of influenza A virus from eight plasmids, PNAS, May 23, 2000, vol. 97, No. 11, pp. 6108-6113.
Yallop et al., "PER.C6® Cells for the Manufacture of Biopharmaceutical Proteins," Modern Biopharmaceuticals, ED. J. Knablein, 2005, Wiley-VCH Verlag GmbH & Co. KGaA, Weinheim, Germany.
Bout et al., "Improved helper cells for RCA-free production of El-deleted recombinant adenovirus vectors," Cancer Gene Therapy, 1996, pp. S24, vol. 3, No. 6.
Bout et al., "Production of RCA-free batches of E1-deleted recombinant adenoviral vectors on PER.C6," Nucleic Acids Symp. Ser. 1998, XP-002115716, pp. 35-36.
Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.

Carroll et al., Abstract, Differential Infection of Receptor-modified Host Cells by Receptor-Specific Influenza Viruses, Virus Research, Sep. 1985, pp. 165-179, vol. 3, No. 2.

Cronan, Abstract, Biotination of Proteins in-vivo a post-translational modification to label purify and study proteins, Journal of Biological Chemistry, Jun. 25, 1990, pp. 10327-10333, vol. 265, No. 18.

Endo et al., Growth of Influenza A Virus in Primary, Differentiated Epithelial Cells Derived from Adenoids, Journal of Virology, Mar. 1996, pp. 2055-2058, vol. 70, No. 3.

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Ghosh-Choudhury et al., Protein IX, a minor component of the human adenovirus capsid, is essential for the packaging of the full length genomes, The EMBO Journal, 1987, pp. 1733-1739, vol. 6, No. 6.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Hollister et al., Stable expression of mammalian beta 1,4-galactosyltransferase extends the N-glycosylation pathway in insect cells, Glycobiology, 1998, pp. 473-480, vol. 8, No. 5, IRL Press, United Kingdom.

Jenkins et al., Getting the glycosylation right: Implications for the biotechnology industry, Nature Biotechnology, Aug. 1996, pp. 975-981, vol. 14, No. 8, Nature Publishing, US.

Louis et al., Cloning and Sequencing of the Cellular—Viral Junctions from the Human Adenovirus Type 5 Transformed 293 Cell Line, Virology, 1997, pp. 423-429, vol. 233.

Merten et al., Production of Influenza Virus in Cell Cultures for Vaccine Preparation, Exp Med Biol., 1996, pp. 141-151, vol. 397.

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

NCBI Entrez Nucleotide accession No. X02996 J01967 J01968 J01970 J01971 J01972 J01974 J01976 J01977 J01978 J01979 K00515 V00025 V00026 V00027 V00029.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Pau et al., Abstract, The human cell line PER.C6 provides a new manufacturing system for the production of influenza vaccines, Vaccine, Mar. 21, 2001, pp. 2716-2721, vol. 19, No. 17-19.

Paul et al., Increased Viral Titer Through Concentration of Viral Harvests from Retroviral Packaging Lines, Human Gene Therapy, 1993, pp. 609-615, vol. 4.

Pazur et al., Abstract, Oligosaccharides as immunodeterminants of erythropoietin for two sets of anti-carbohydrate antibioties, Journal of Protein Chemistry, Nov. 2000, pp. 631-635, vol. 19, No. 8.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Schiedner et al., Abstract, Efficient transformation of primary human amniocytes by E1 functions of Ad5: generation of new cell lines for adenoviral vector production, 2000, Hum. Gene Ther. 11, 2105-2116.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-1953, vol. 84, No. 9.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Yu et al., "Enhanced c-erbB-2/neu expression in human ovarian cancer cells correlates with more severe malignancy that can be suppressed by EIA," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

* cited by examiner

FIG. 13
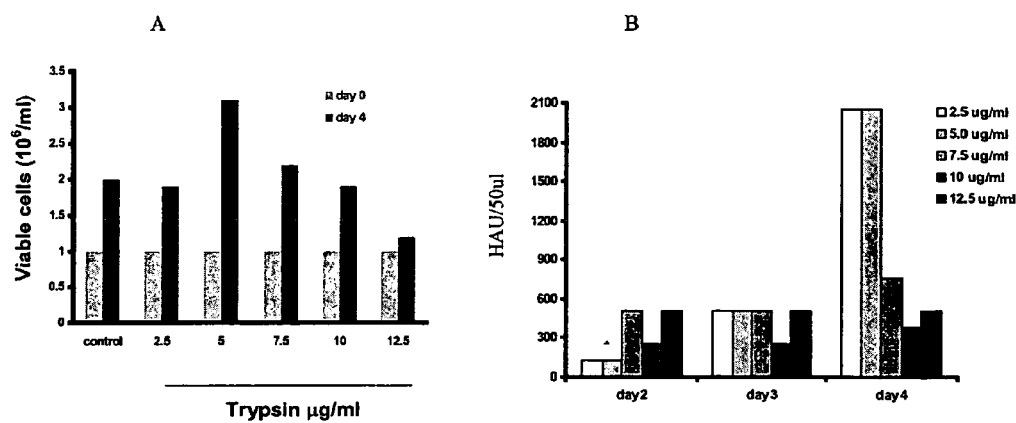
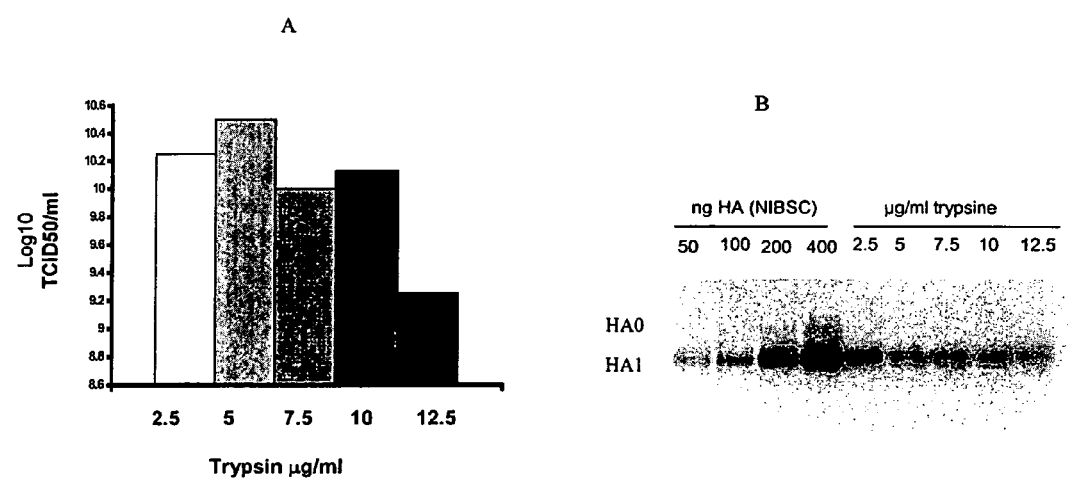
FIG. 14

FIG. 15
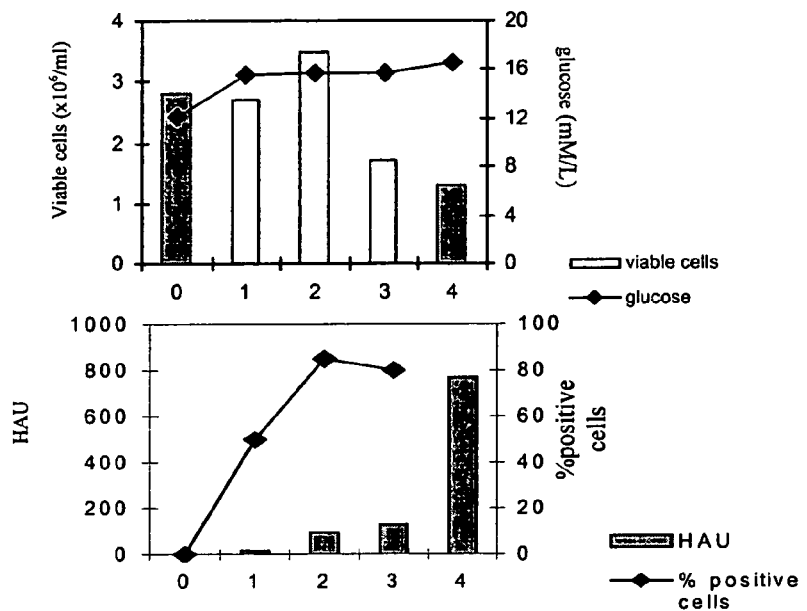
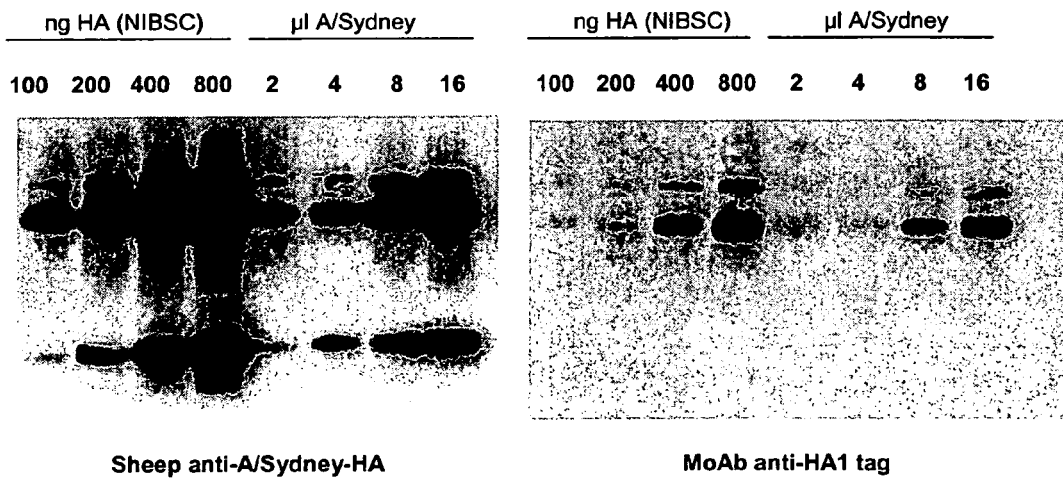
Sheep anti-A/Sydney-HA    MoAb anti-HA1 tag
FIG. 16

FIG. 17
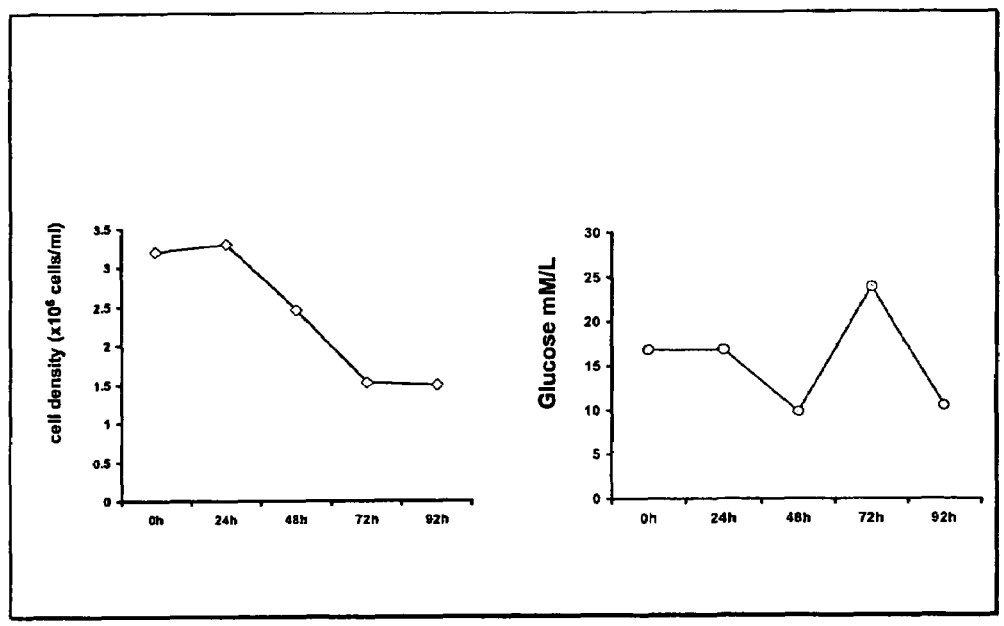
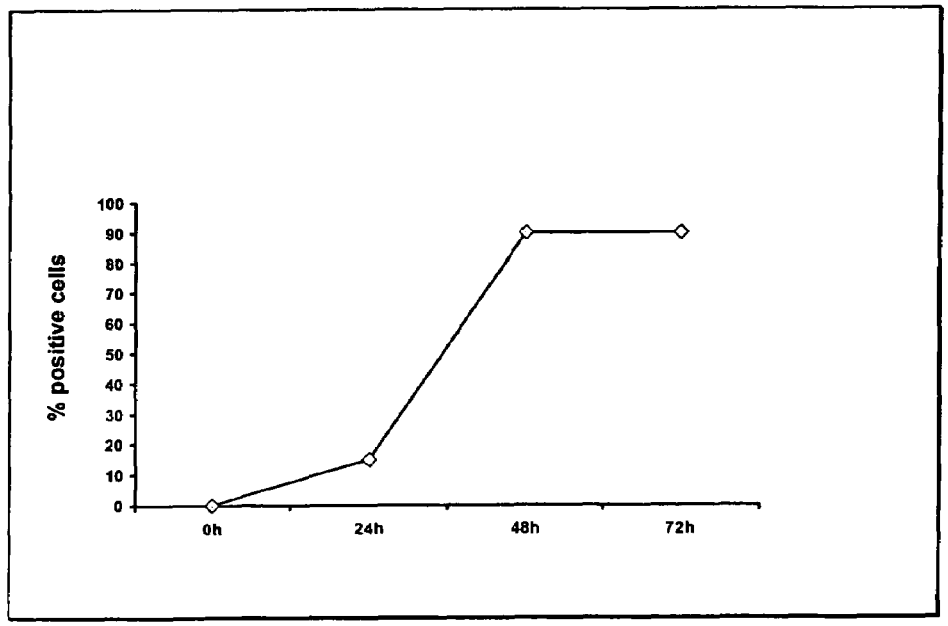
FIG. 18

FIG. 19
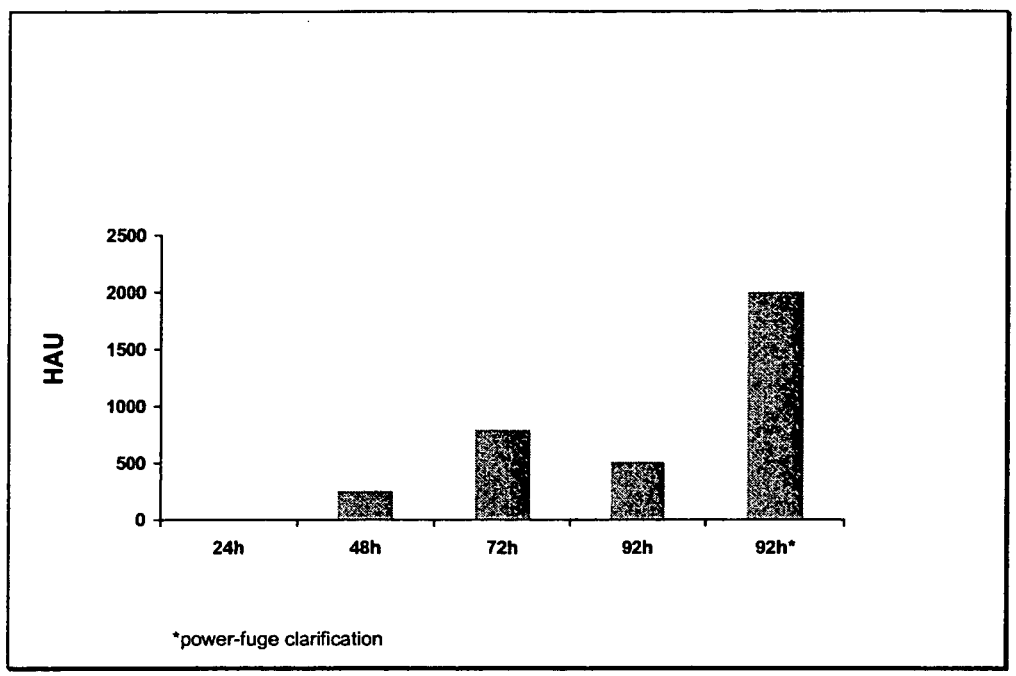
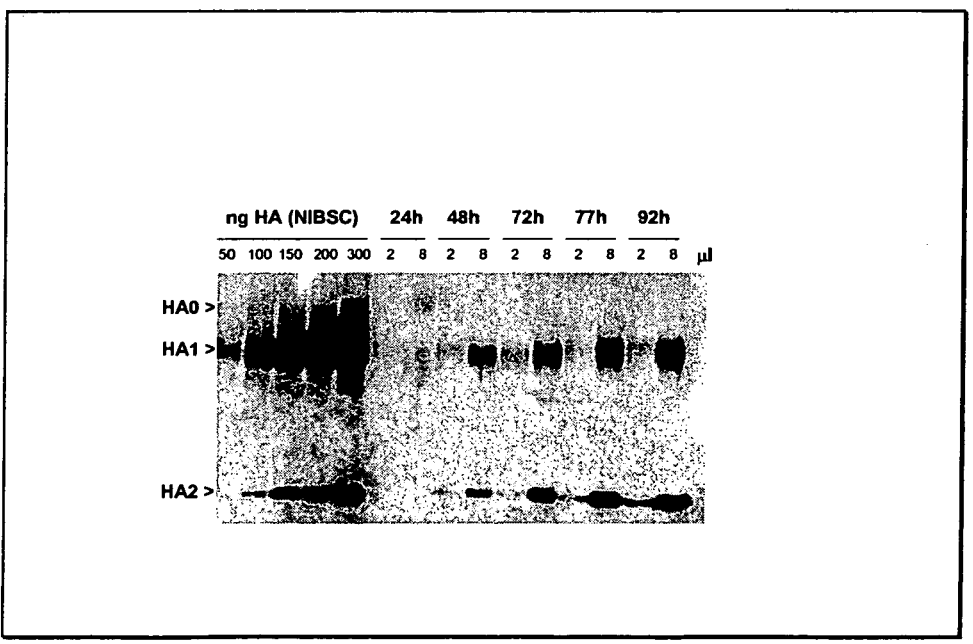
FIG. 20

|  | unconcentrated | 20x concentrated |
|---|---|---|
| HAU | 2048 | 65384 |
| pfu/ml | 1.80E+07 | 1.89E+08 |

FIG. 21

FIG. 25
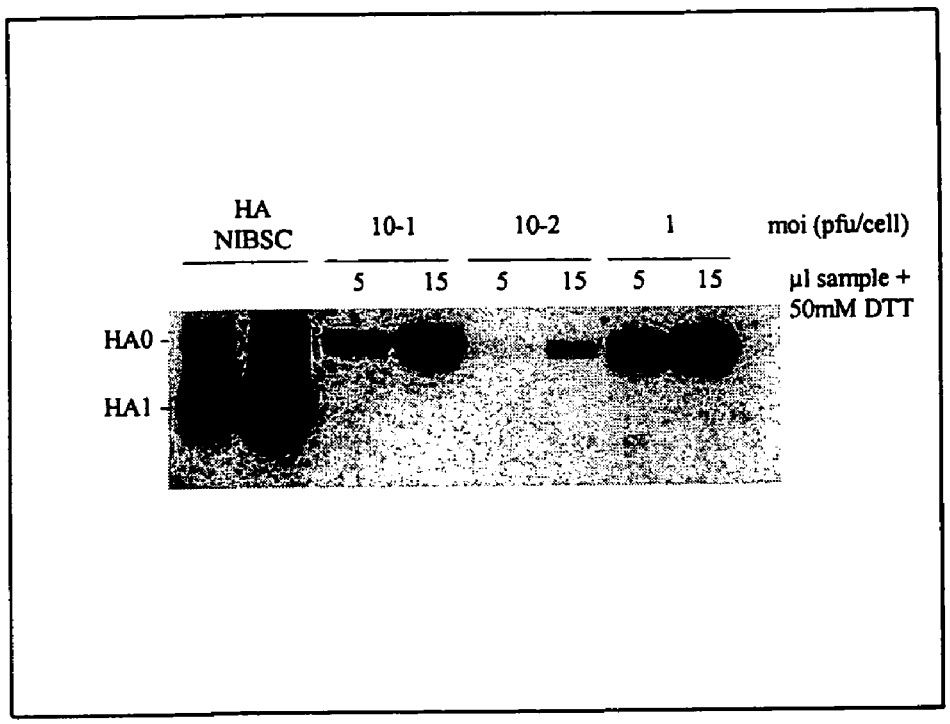
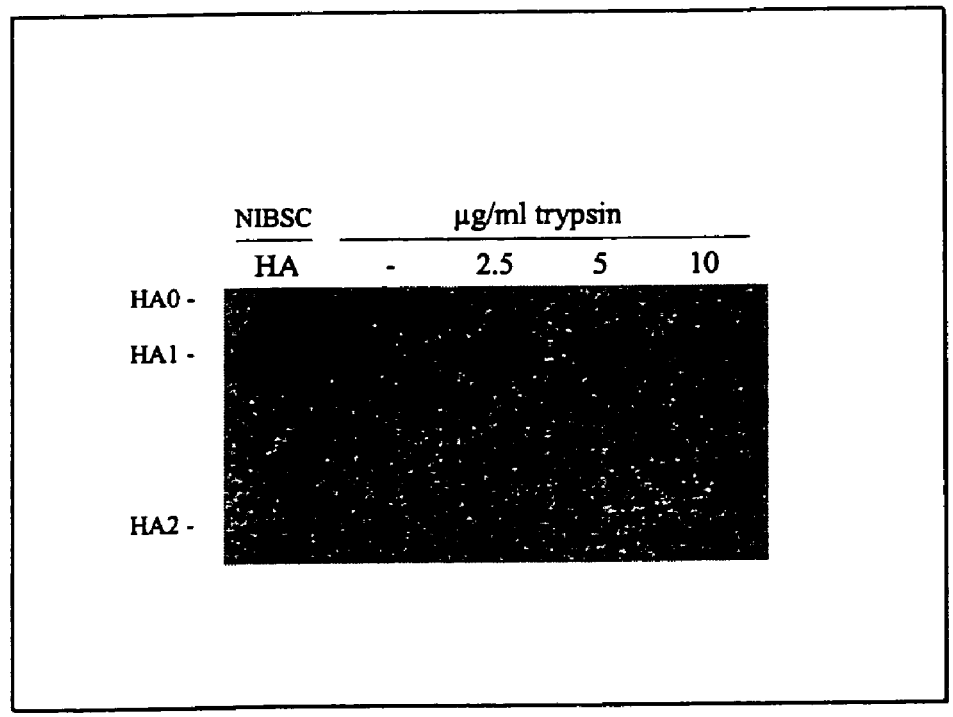
FIG. 26A

FIG. 26B

Detection of trypsin activity in B/Harbin infection supernatants

FIG. 27

Influenza virus on PER.C6™

- H3N2 strains
  A/Sydney/5/97*
  A/Johannesburg/33/94*
  A/Nanchang/933/95*
  A/Wuhan/359/95*
  A/Moscow/10/99*
  A/Panama/2007/99

- B strains
  B/Harbin/7/94
  B/Yamanashi/166/98
  B/Beijing/184/93*
  B/Shandong/7/97

- H1N1 strains
  A/Beijing/262/95
  X-127 A/Beijing reassortant
  A/New Caledonia/20/99
  A/Johannesburg/282/96
  A/Texas/36/91

- Avian strains
  A/Duck/Singapore-Q/F119-3/97*

*Difficult growth on eggs*

ND OF VACCINES

SEQUENCE LISTING

<160> NUMBER OF SEQ ID NOS: 1

<210> SEQ ID NO 1
<211> LENGTH: 3052
<212> TYPE: DNA
<213> ORGANISM: Adenoviridae

<400> SEQUENCE: 1

```
cgtgtagtgt atttataccc ggtgagttcc tcaagaggcc actcttgagt gccagcgagt        60
agagttttct cctccgagcc gctccgacac cgggactgaa aatgagacat attatctgcc       120
acggaggtgt tattaccgaa gaaatggccg ccagtctttt ggaccagctg atcgaagagg       180
tactggctga taatcttcca cctcctagcc attttgaacc acctaccctt cacgaactgt       240
atgatttaga cgtgacggcc cccgaagatc ccaacgagga ggcggtttcg cagattttc        300 ccgactctgt aatgttggcg gtgcaggaag ggattgactt actcactttt ccgccggcgc       360
ccggttctcc ggagccgcct caccttttccc ggcagcccga gcagccggag cagagagcct     420
tgggtccggt ttctatgcca aaccttgtac cggaggtgat cgatcttacc tgccacgagg       480
ctggctttcc acccagtgac gacgaggatg aagagggtga ggagtttgtg ttagattatg       540
tggagcaccc cgggcacggt tgcaggtctt gtcattatca ccggaggaat acggggggacc     600 cagatattat gtgttcgctt tgctatatga ggacctgtgg catgtttgtc tacagtaagt       660
gaaaattatg ggcagtgggt gatagagtgg tgggtttggt gtggtaattt ttttttttaat     720 ttttacagtt ttgtggttta aagaattttg tattgtgatt ttttaaaag gtcctgtgtc       780 tgaacctgag cctgagcccg agccagaacc ggagcctgca agacctaccc gccgtcctaa       840
aatggcgcct gctatcctga gacgcccgac atcacctgtg tctagagaat gcaatagtag       900
tacggatagc tgtgactccg gtccttctaa cacacctcct gagatacacc cggtggtccc       960
gctgtgcccc attaaaccag ttgccgtgag agttggtggg cgtcgccagg ctgtggaatg      1020
tatcgaggac ttgcttaacg agcctgggca accttttggac ttgagctgta aacgccccag      1080
gccataaggt gtaaacctgt gattgcgtgt gtggttaacg cctttgtttg ctgaatgagt      1140
tgatgtaagt ttaataaagg gtgagataat gtttaacttg catggcgtgt taaatggggc      1200
ggggcttaaa gggtatataa tgcgccgtgg gctaatcttg gttacatctg acctcatgga      1260
ggcttgggag tgtttggaag attttttctgc tgtgcgtaac ttgctggaac agagctctaa     1320
cagtacctct tggttttgga ggtttctgtg gggctcatcc caggcaaagt tagtctgcag      1380
aattaaggag gattacaagt gggaatttga agagctttg aaatcctgtg gtgagctgtt       1440
```

-continued

```
tgattctttg aatctgggtc accaggcgct tttccaagag aaggtcatca agactttgga    1500
tttttccaca ccggggcgcg ctgcggctgc tgttgctttt ttgagtttta taaaggataa    1560
atggagcgaa gaaacccatc tgagcggggg gtacctgctg gattttctgg ccatgcatct    1620
gtggagagcg gttgtgagac acaagaatcg cctgctactg ttgtcttccg tccgcccggc    1680
gataataccg acggaggagc agcagcagca gcaggaggaa gccaggcggc ggcggcagga    1740
gcagagccca tggaacccga gagccggcct ggaccctcgg gaatgaatgt tgtacaggtg    1800
gctgaactgt atccagaact gagacgcatt ttgacaatta cagaggatgg gcagggcta    1860
aaggggtaa agagggagcg gggggcttgt gaggctacag aggaggctag gaatctagct    1920
tttagcttaa tgaccagaca ccgtcctgag tgtattactt ttcaacagat caaggataat    1980
tgcgctaatg agcttgatct gctggcgcag aagtattcca tagagcagct gaccacttac    2040
tggctgcagc caggggatga ttttgaggag gctattaggg tatatgcaaa ggtggcactt    2100
aggccagatt gcaagtacaa gatcagcaaa cttgtaaata tcaggaattg ttgctacatt    2160
tctgggaacg gggccgaggt ggagatagat acggaggata gggtggcctt tagatgtagc    2220
atgataaata tgtggccggg ggtgcttggc atggacgggg tggttattat gaatgtaagg    2280
tttactggcc ccaattttag cggtacggtt ttcctggcca ataccaacct tatcctacac    2340
ggtgtaagct tctatgggtt taacaatacc tgtgtggaag cctggaccga tgtaagggtt    2400
cggggctgtg ccttttactg ctgctggaag ggggtggtgt gtcgcccaa aagcagggct    2460
tcaattaaga aatgcctctt tgaaaggtgt accttgggta tcctgtctga gggtaactcc    2520
agggtgcgcc acaatgtggc ctccgactgt ggttgcttca tgctagtgaa aagcgtggct    2580
gtgattaagc ataacatggt atgtggcaac tgcgaggaca gggcctctca gatgctgacc    2640
tgctcggacg gcaactgtca cctgctgaag accattcacg tagccagcca ctctcgcaag    2700
gcctggccag tgtttgagca taacatactg acccgctgtt ccttgcattt gggtaacagg    2760
agggggtgt tcctaccta ccaatgcaat ttgagtcaca ctaagatatt gcttgagccc    2820
gagagcatgt ccaaggtgaa cctgaacggg gtgtttgaca tgaccatgaa gatctggaag    2880
gtgctgaggt acgatgagac ccgcaccagg tgcagaccct gcgagtgtgg cggtaaacat    2940
attaggaacc agcctgtgat gctggatgtg accgaggagc tgaggcccga tcacttggtg    3000
ctggcctgca cccgcgctga gtttggctct agcgatgaag atacagattg ag           3052
```

PRODUCTION OF VACCINES

CROSS-REFERENCE TO RELATED APPLICATIONS

This application is a continuation-in-part of U.S. patent application Ser. No. 09/722,867, filed Nov. 27, 2000, pending, which is a continuation-in-part of U.S. patent application Ser. No. 09/449,854 filed on Nov. 26,1999, the entire contents of each of which are incorporated by this reference.

TECHNICAL FIELD

This invention relates generally to biotechnology, and more particularly to the development and manufacture of vaccines. In particular, the invention relates to the production of viral proteins and/or viruses using a mammalian (e.g., human) cell for the production of viruses growing in eukaryotic, especially mammalian and human, cells. The invention is useful for the production of vaccines to aid in protection against viral pathogens for vertebrates, such as mammals.

BACKGROUND

Presently, vaccination is the most important route of dealing with viral infections. Although a number of antiviral agents are available, typically, these agents have limited efficacy. Administering antibodies against a virus may be a good way of dealing with viral infections once an individual is infected (passive immunization). Typically, human or humanized antibodies hold promise for dealing with a number of viral infections, but the most efficacious and safe way of dealing with virus infection presently is, and probably will be, prophylaxis through active immunizations. Active immunization is generally referred to as "vaccination." Vaccines comprise at least one antigenic determinant (typically of a virus), preferably a number of different antigenic determinants of at least one virus or other pathogen, for instance, by incorporating in the vaccine at least one (viral) polypeptide or protein derived from a virus (subunit vaccines).

Typically, vaccines include adjuvants in order to enhance the immune response. Use of adjuvants is also possible for vaccines that use whole virus (pathogen), for instance, when the virus is inactivated. Another possibility is the use of live, but attenuated, virus. A further possibility is the use of wild-type ("wt") virus, for instance, in cases where adult individuals are not in danger of infection but infants are and may be protected through maternal antibodies and the like.

Producing vaccines is not always an easy procedure. In some cases, the production of viral material is on eggs, which may lead to materials that are difficult to purify and require extensive safety measures against, for instance, contamination. Likewise, production on bacteria or yeast, which is sometimes an alternative for eggs, can require many purification and safety steps.

Production on mammalian cells would be an alternative, but the mammalian cells used thus far have required, for instance, the presence of serum and/or adherence to a solid support for growth. In the first case, again purification and safety and, for example, the requirement of protease to support the replication of some viruses, becomes an issue. In the second case, high yields and ease of production become a further issue. The present invention overcomes at least a number of the problems encountered with the production systems for production of viruses and/or viral proteins for vaccine purposes of the systems of the prior art.

BRIEF SUMMARY OF THE INVENTION

The invention includes a novel human immortalized cell line for the purpose of propagating, harvesting and producing virus. PER.C6 cells (see, e.g., U.S. Pat. No. 5,994,128 to Bout et al., also deposited under No. 96022940 at the European Collection of Animal Cell Cultures at the Centre for Applied Microbiology and Research) were generated by transfection of primary human embryonic retina cells using a plasmid that contained the adenovirus ("Ad") serotype 5 (Ad5) E1A- and E1B-coding sequences (Ad5 nucleotides 459-3510) (SEQ ID NO:1) under the control of the human phosphoglycerate kinase (PGK) promoter.

The following features make PER.C6 or a derivative thereof particularly useful as a host for virus production: it is a fully characterized human cell line; it was developed in compliance with good laboratory practices; it can be grown as a suspension culture in defined serum-free medium, devoid of any human or animal serum proteins; its growth is compatible with roller bottles, shaker flasks, spinner flasks and bioreactors, with doubling times of about 35 hours.

Influenza Epidemiology

Influenza viruses, members of the family of Orthomyxoviridae, are the causative agents of annual epidemics of acute respiratory disease. In the U.S. alone, 50 million Americans get the flu each year. Estimated deaths worldwide (1972-1992) are 60,000 (CDC statistics). There have been three major cases of pandemics of influenza, namely in 1918 (Spanish flu, estimated 40 million deaths), in 1957 (Asian flu, estimated 1 million deaths), and in 1968 (Hong-Kong flu, estimated 700,000 deaths).

Infections with influenza viruses are associated with a broad spectrum of illnesses and complications that result in substantial worldwide morbidity and mortality, especially in older people and patients with chronic illness. Vaccination against influenza is most effective in preventing the often fatal complications associated with this infection (Murphy, B. R. and R. G. Webster 1996). The production of influenza virus on the diploid human cell line MRC-5 has been reported (Herrero-Euribe L. et al. 1983). However, the titers of influenza virus were prohibitively low.

Strains of Influenza Virus

Present day flu vaccines contain purified hemagglutinin and neuraminidase of Influenza virus A and B. The three viruses that represent epidemiologically important strains are Influenza A (H1N1), Influenza A (H3N2) and Influenza B. The division into A and B types is based on antigenic differences between their nucleoprotein (NP) and matrix (M) protein antigen. The Influenza A virus is further subdivided into subtypes based on the antigenic composition (sequence) of hemagglutinin (H1-H15) and neuraminidase (N1-N9) molecules. Representatives of each of these subtypes have been isolated from aquatic birds, which probably are the primordial reservoir of all influenza viruses for avian and mammalian species. Transmission has been shown between pigs and humans and, recently (H5N1), between birds and humans.

Influenza Vaccines

Three types of inactivated influenza vaccine are currently used in the world: whole virus, split product, and surface antigen or "subunit" vaccines. These vaccines all contain the surface glycoproteins, hemagglutinin (HA) and neuraminidase (NA) of the influenza virus strains that are expected to circulate in the human population in the upcoming season. These strains, which are incorporated into the vaccine, are grown in embryonated hens' eggs and the viral particles are subsequently purified before further processing.

The need for the yearly adjustment of influenza vaccines is due to antigen variation caused by processes known as "antigenic drift" and "antigenic shift."

"Antigenic drift" occurs by the accumulation of a series of point mutations in either the H or N protein of a virus resulting in amino acid substitutions. These substitutions prevent the binding of neutralizing antibodies induced by previous infection and the new variant can infect the host.

"Antigenic shift" is the appearance of a new subtype by genetic re-assortment between animal and human Influenza A viruses. The pandemic strains of 1957 (H2N2) and 1968 (H3N2) are examples of re-assorted viruses by which avian H and/or N genes were introduced in circulating human viruses that subsequently spread among the human population.

Based on the epidemiological surveys by over one hundred National Influenza Centres worldwide, the World Health Organization (WHO) yearly recommends the composition of the influenza vaccine, usually in February for the northern hemisphere and in September for the southern hemisphere. This practice limits the time window for production and standardization of the vaccine to a maximum of nine months.

If an urgent demand arises for many doses of vaccine, for example, when a novel subtype of Influenza A virus arises by antigenic shift or antigenic drift, limited availability of eggs may hamper the rapid production of vaccine. Further disadvantages of this production system are the lack of flexibility, the risk of the presence of toxins, and the risks of adventitious viruses, particularly retroviruses, and concerns about sterility. These disadvantages present a serious problem in today's practice of influenza vaccine production on embryonated hens' eggs.

Therefore, the use of a cell culture system for influenza vaccine production would be an attractive alternative. Influenza viruses can be grown on a number of primary cells, including monkey kidney, calf kidney, hamster kidney and chicken kidney. Yet, their use for vaccine production is impractical, due to the need to re-establish cultures from these primary cells for each preparation of a vaccine. Therefore, the use of continuous immortalized cell lines for influenza vaccine production is an attractive alternative.

The use of culture systems was facilitated by the realization that the proteolytic cleavage of HA into its two subunits (HA1 and HA2) is required for influenza virus infectivity and can be obtained by adding trypsin. Including trypsin permits replication and plaque formation in Madin-Darby canine kidney (MDCK) cells (Tobita et al. 1975).

The MDCK cell line was recently shown to support the growth of influenza virus for vaccine production (Brand et al. 1996 and 1997, Palache et al. 1997). The use of trypsin requires growth of the MDCK cells in serum-free tissue culture medium (MDCK-SF1). However, MDCK cells are currently not approved as a substrate for production of influenza virus.

Importantly, any non-human system for producing influenza vaccines has an inherent drawback, known as "adaptation." Human Influenza A and B viruses both carry mutations in HA, due to adaptation in embryonated hens' eggs. These mutations result in altered antigenicity (Newman et al. 1993, Williams and Robertson 1993, Robertson et al. 1994, Gubareva et al. 1994, Schild et al. 1993, Robertson et al. 1987, Kodihalli et al. 1995). In humans, immunization with vaccines containing HA bearing an egg-adaptation mutation induces less neutralizing antibody to virus than a non-egg adapted HA (Newman et al. 1993).

Human influenza viruses propagated in canine cells, such as MDCK cells, also show adaptation, albeit to a lesser extent. Such viruses resemble the original human isolates more closely than egg-derived viruses (Robertson et al. 1990).

Furthermore, evidence exists that host-specific changes in NA and host-specific phosphorylation patterns of NA can affect the replication of Influenza viruses (Schulman and Palese 1977; Sugiara and Ueda 1980; Kistner et al. 1976).

Therefore, it would clearly be advantageous to avoid adaptation or other host-induced changes of influenza virus, possibly resulting in a more homogeneous population of viruses, rendering the ultimate vaccine more effective.

The present invention provides human cells used as a substrate for the production of high titers of influenza virus suitable for the development of vaccines.

Rotavirus and Vaccines Therefor

Rotaviruses are the most important cause of severe dehydrating gastroenteritis in young children worldwide. In developing countries, infections with rotaviruses reportedly lead to over 800,000 deaths annually. In the United States alone, estimated costs of health care due to rotavirus infections exceed 1 billion U.S. dollars per year.

Rotaviruses, members of the family of Reoviridae, are double stranded RNA viruses consisting of eleven RNA segments, each coding for a structural or non-structural viral protein (VP). This inner core of the virus comprises four VPs: VP1, 2, 3 and 6. These VP determine the three main antigenic properties of HRV—group, subgroup, and serotype. Seven antigenically distinct groups (denominated A through G) have been identified that are encoded by the VP6. Infection with human rotavirus (HRV) is predominantly caused by group A rotaviruses, with serotypes 1-4 accounting for 95% of clinical illness. Natural disease protection is serotype-specific. Group A is further classified into subgroups I and II.

The double layer outer shell forming the viral capsid consists of two viral proteins, VP4 and VP7, that are the neutralization antigens involved in protective immunity and that determine the serotype, although the VP4 plays a minor role in serotype determination. During co-infection with different serotypes, the segmented genomes readily undergo genetic re-assorting, a property that has been used to create a vaccine (Marsha et al. 1999).

Given the worldwide prevalence of rotavirus-associated infant morbidity and mortality, large scale vaccination against rotavirus is considered the most effective way to combat this virus. The goal of vaccination would not be to prevent the disease but to reduce its morbidity, especially during the first few years of life.

The only effective vaccine available at present is a live, attenuated, orally delivered vaccine based on the re-assortment of RNA segments of human rotaviruses, encoding the VP7s of serotypes 1, 2 and 4 in a Rhesus rotavirus supplying the attenuated background together with the VP7 of serotype 3. Vaccination with this human/rhesus reassortant tetravalent vaccine (RRV-TV), although highly effective in preventing severe gastroenteritis, is associated with intussusception, a bowel obstruction disease. For that reason, this vaccine is no longer in use.

Means and methods are disclosed herein for producing a virus and/or viral protein in a cell, preferably using a defined synthetic medium, and for purifying the virus and/or components thereof from the cell and/or culture medium. Pharmaceutical compositions containing virus or its components and methods for manufacturing and recovering and/or purifying them are provided.

BRIEF DESCRIPTION OF THE FIGURES

FIG. 13 consists of Portions A and B depicting effect of trypsin-EDTA on (A) PER.C6 cells viability and (B) biological activity of the virus. Cell viability was measured after trypan-blue staining. HAU titers were measured as described and given per 50 µl.

FIG. 14 consists of Portions A and B depicting effect of trypsin-EDTA on virus infectivity titers and HA protein content after influenza infection of PER.C6 cells with A/Sydney/5/97. (A) The infectivity assay was carried out by inoculating, in quadruplicate, MDCK cells with a total of 100 µl of ten-fold serially diluted virus-containing supernatants, in serum-free medium with trypsin-EDTA (4 µg/ml). After seven days, supernatant of these cultures were tested for HA activity. The infectious virus titers were calculated according to the method of Spearnan-Karber (1931). (B) Western blot analysis of the A/Sydney/5/97 HA protein. Harvesting of viral proteins was carried out by disruption and denaturation of proteins using an SDS-containing lysis buffer. The electrophoretic run was performed on a 10% SDS/PAGE gel under reducing conditions. Separated proteins were probed with the specific anti-A/Sydney-HA antisera. Increasing amounts of the positive control A/Sydney HA antigen (left four lanes) and 10 µl of PER.C6 cells supernatants of the indicated trypsin incubated samples (right five lanes) were loaded.

FIG. 15 consists of an upper and lower portion and depict PER.C6 cells viability, glucose concentration, and growth kinetics of A/Sydney/5/97 in a hollow fiber perfusion system.

FIG. 16 consists of a right and left portion and depicts the characterization and quantification of Influenza Virus A/Sydney/5/97 propagated on PER.C6 in a hollow fiber perfusion system. SDS-PAGE and Western blots were done as described in legend to FIG. 14 for the Sheep anti-A/Sydney-HA antibody. The monoclonal antibody anti-HA-tag (HA probe F7) mouse monoclonal (Santa Cruz) was used in 1:1000 dilution. As a second antibody, a goat anti-mouse-HRP-conjugated antibody (Biorad), in 1:7500 dilution was used.

FIG. 17 consists of a right and left graph and depicts PER.C6 cells viability (left panel) and glucose concentration (right panel) in a 12 liter bioreactor up to 92 hours after viral infection using A/Sydney/5/97 virus.

FIG. 18 is a graph depicting the infection of PER.C6 with A/Sydney/5/97 in a 10 liter cell suspension in a 12 liter bioreactor. Kinetics of virus replication as measured by immunofluorescence assay are given in percentages of positively stained cells.

FIG. 19 is a bar graph depicting infection of PER.C6 cells with A/Sydney/5/97 in a 10 liter cell suspension in a 12 liter bioreactor. Kinetics of virus replication as measured by Hemagglutination assay are given in HAUs during several days after viral infection. The bar depicted with an asterisk is the number of HAUs obtained after Powerfuge™ clarification as described in the text.

FIG. 20 is a Western blot following infection of PER.C6 with A/Sydney/5/97 virus in a 10 liter cell suspension in a 12 liter bioreactor. Shown is the characterization and quantification of the Influenza virus A/Sydney/5/97 HA polypeptide. SDS/PAGE and Western blot were done as described with respect to FIG. 14. The different subunits (HA1 and HA2) and the non-cleaved HA0 proteins are depicted by arrow heads. The HA obtained from NIBSC served as a positive control.

FIG. 21 shows the determination of HAUs and pfu/ml after infection of PER.C6 with A/Sydney/5/97 in a 10 liter cell suspension in a 12 liter bioreactor. The infection was followed by Down Stream Processing (DSP). The recovery of viral yields after hollow fiber ultra-filtration (20-fold concentration) is also shown.

FIG. 25 is a Western blot analysis of uncleaved A/Sydney/5/97 HA0 protein. Positive staining proteins are detected after incubation with the specific anti-A/Sydney antisera obtained from NIBSC and described as in the legend of FIG. 14 and in the text.

FIG. 26A is a Western blot analysis of A/Sydney/5/97-derived HA0 protein digested with trypsin. Proteins are detected after incubation with the specific anti-A/Sydney antisera. On the left, a standard cleaved A/Sydney HA and on the right, HA0 treated with increasing amount of trypsin.

FIG. 26B is a determination of trypsin activity in the culture supernatant of an Influenza B/Harbin production run, using HA0 of Influenza A/Sydney/5/97 as substrate. Western blot analysis of HA0 cleavage products HA1 and HA2 as visualized by anti-Influenza A/Sydney/5/97 HA-specific antisera is mentioned in legend to FIG. 14.

FIG. 27 is a Western blot analysis of A/Sydney HA0 digested with N-glycosydase F. Proteins are detected after incubation with the specific anti-A/Sydney antisera. The protein band depicted with an asterisk is the de-glycosylated product.

DETAILED DESCRIPTION OF THE INVENTION

Figure 1:
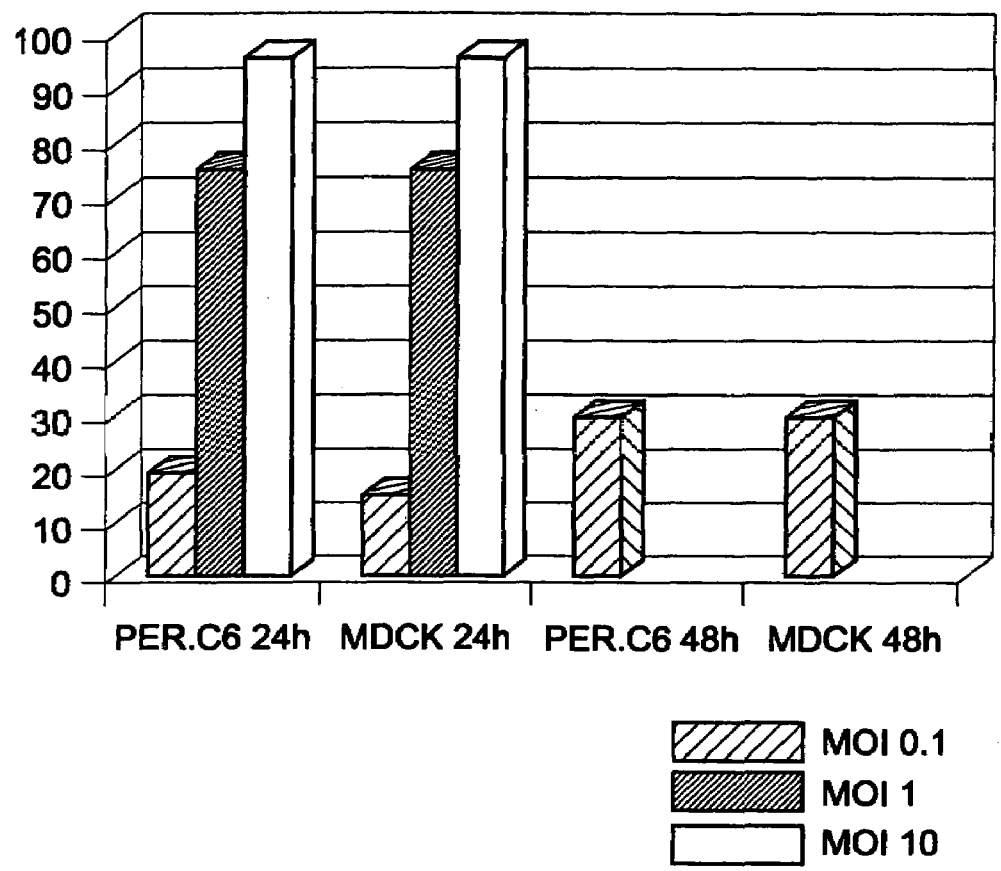
FIG. 1 is a graph depicting percentage of infected cells (positive cells) viewed microscopically after immunofluorescence assay versus percentage of dead cells measured via FACS after propidium iodide staining, at multiplicities of infection (mois) of $10^{-3}$ and $10^{-4}$. Poor viability of the cells from samples derived from infection at moi $10^{-3}$ did not give rise to reliable data.
Figure 2:
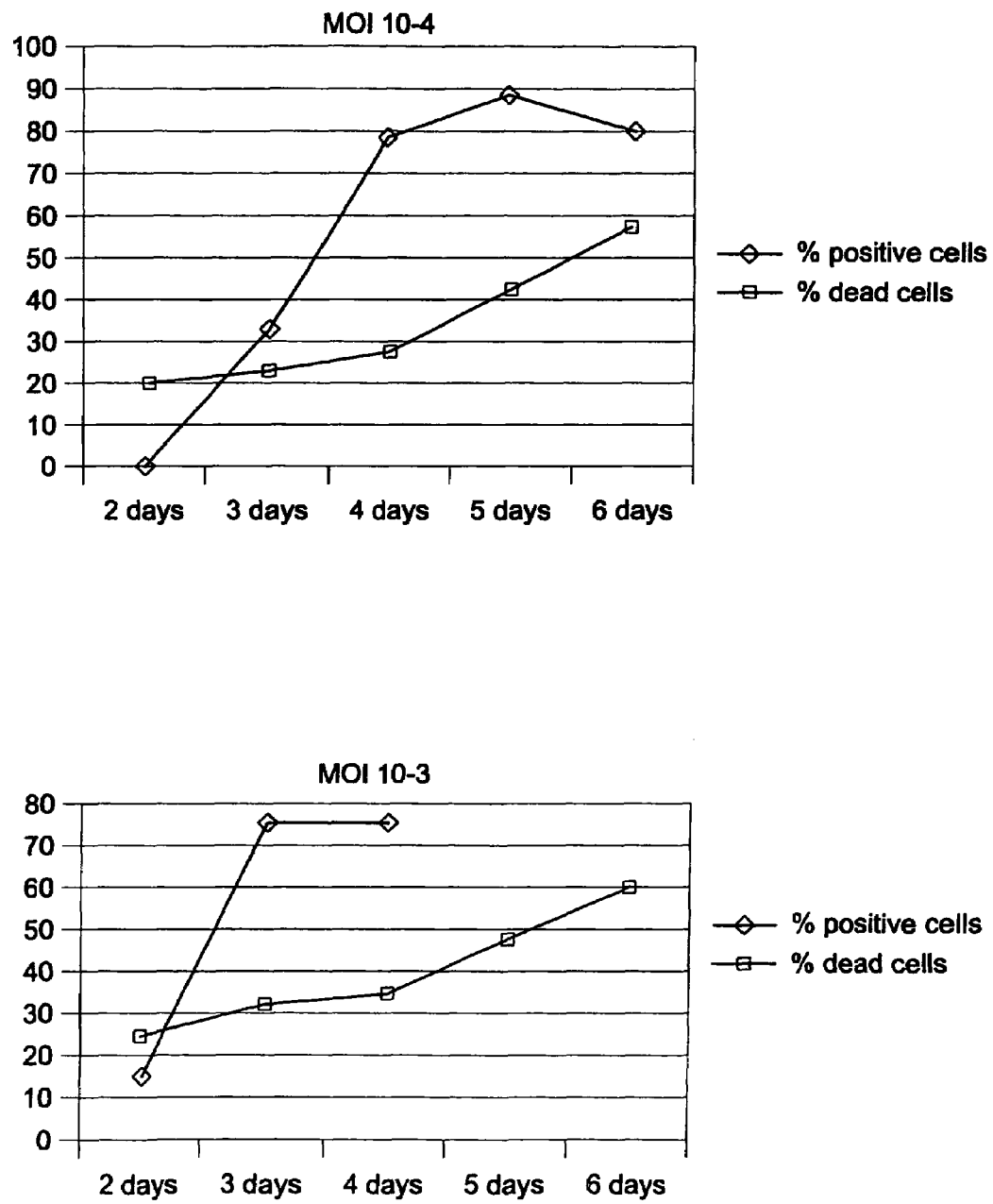
FIG. 2 consists of two graphs depicting percentage of infected cells viewed microscopically after immunofluorescence assay. Samples derived from infection at moi 10 and 1, at 48 hours post-infection are not shown, because of full CPE.
Figure 3:
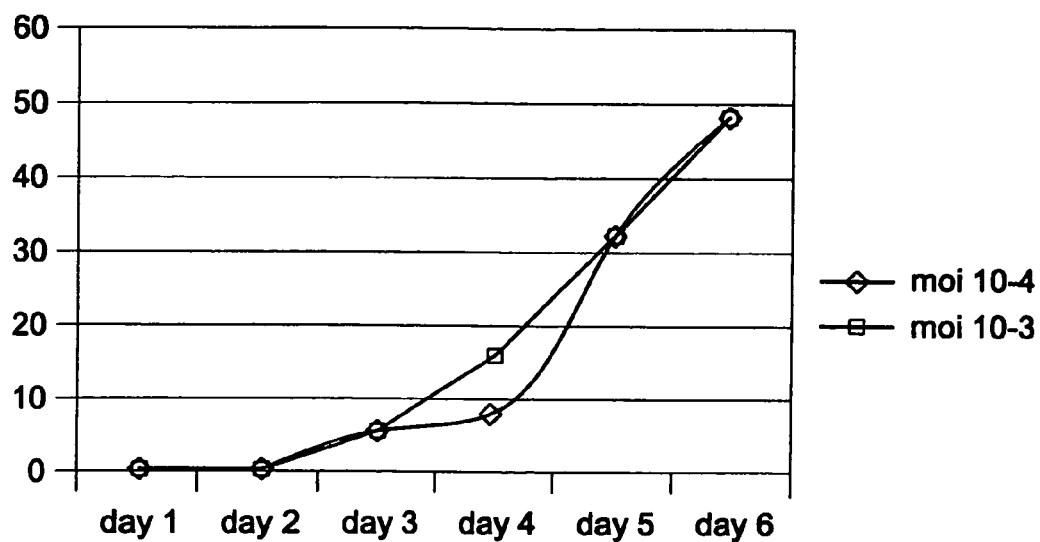
FIG. 3 is a graph depicting kinetics of virus propagation measured in hemagglutinating units (HAU) from day 1 through day 6 after infection.

The invention provides a method for producing a virus and/or viral proteins, other than adenovirus or adenoviral proteins, for use as a vaccine comprising: providing a cell with at least a sequence encoding at least one gene product of the E1 gene, or a functional derivative thereof, of an adenovirus; providing the cell with a nucleic acid encoding the virus or the viral proteins; culturing the cell in a suitable medium and allowing for propagation of the virus or expression of the viral proteins; and harvesting the virus and/or viral proteins from the medium and/or the cell.

Heretofore, few (if any) human cells have been found that were suitable to produce viruses and/or viral proteins for use as vaccines in any reproducible and scalable manner, in sufficiently high yields, and/or easily purifiable. We have now found that cells having adenoviral E1 sequences (preferably in their genome) are capable of sustaining the propagation of viruses in significant amounts.

A preferred cell according to the invention is derived from a human primary cell, preferably a cell which is immortalized by a gene product of the E1 gene. In order to be able to grow a primary cell, it, of course, needs to be immortalized. A good example of such a cell is one derived from a human embryonic retinoblast.

In cells according to the invention, it is important that the E1 gene sequences are not lost during the cell cycle. It is, therefore, preferred that the sequence encoding at least one gene product of the E1 gene is present in the genome of the human cell.

For safety reasons, care is best taken to avoid unnecessary adenoviral sequences in the cells. It is thus another embodiment of the invention to provide cells that do not produce adenoviral structural proteins. However, in order to achieve large scale (continuous) virus production through cell culture, it is preferred to have cells capable of growing without needing anchorage. Preferred cells according to the invention have that capability. To have a clean and relatively safe production system from which it is easy to recover and, if desired, purify the virus, it is preferred to have a method according to the invention wherein the human cell comprises no other adenoviral sequences. The most preferred cell for the methods and uses of the invention is the previously identified PER.C6 cell or a derivative thereof.

Thus, the invention provides a method of using a cell, wherein the cell further comprises a sequence encoding E2A or a functional derivative, analogue or fragment thereof, preferably a cell wherein the sequence encoding E2A or a functional derivative, analogue or fragment thereof is present in the genome of the human cell and, most preferably, a cell wherein the E2A encoding sequence encodes a temperature-sensitive (ts) mutant E2A.

Furthermore, as previously stated, the invention also provides a method wherein the human cell is capable of growing in suspension.

The invention also provides a method wherein the human cell can be cultured in the absence of serum. A cell according to the invention, in particular PER.C6, preferably has the additional advantage that it can be cultured in the absence of serum or serum components. Thus, isolation is easy, safety is enhanced, and the system has good reliability (synthetic media are the best for reproducibility). The human cells of the invention and, in particular, those based on primary cells, particularly ones based on HER cells, are capable of normal (for humans) post- and peri-translational modifications and assembly. This means that they are very suitable for preparing viral proteins and viruses for use in vaccines.

Thus, the invention provides a method wherein the virus and/or the viral proteins comprise a protein that undergoes post-translational and/or peri-translational modification, such as glycosylation.

A good example of a viral vaccine that has been cumbersome to produce in any reliable manner is influenza vaccine. The invention provides a method wherein the viral proteins comprise at least one of an influenza virus neuraminidase and/or a hemagglutinin. Other viral proteins (subunits) and viruses (wt to be inactivated) or attenuated viruses that may be produced in the methods according to the invention include enterovirus (such as rhinovirus, aphtovirus, or poliomyelitis virus), herpes virus (such as herpes simplex virus, pseudorabies virus or bovine herpes virus), orthomyxovirus (such as influenza virus), a paramyxovirus (such as Newcastle disease virus, respiratory syncitio virus, mumps virus or a measles virus), retrovirus (such as human immunodeficiency virus or a parvovirus or a papovavirus), rotavirus or a coronavirus (such as transmissible gastroenteritis virus), a flavivirus (such as tick-borne encephalitis virus or yellow fever virus), a togavirus (such as rubella virus or Eastern-, Western-, or Venezuelan equine encephalomyelitis virus), a hepatitis-causing virus (such as hepatitis A or hepatitis B virus), a pestivirus (such as hog cholera virus), a rhabdovirus (such as rabies virus), or a Bunyaviridae virus (such as Hantavirus).

In one embodiment, a cell of the invention is useful in the generation of an influenza virus strain that does not grow very efficiently on embryonal eggs.

The invention also includes the use of a human cell having a sequence encoding at least one adenoviral E1 protein or a functional derivative, homolog or fragment thereof in its genome, which cell does not produce structural adenoviral proteins for the production of a virus, or at least one viral protein for use in a vaccine. Of course, for such a use, the cells preferred in the methods according to the invention are also preferred. The invention also provides the products resulting from the methods and uses according to the invention, especially viral proteins and viruses obtainable according to those uses and/or methods, especially when brought in a pharmaceutical composition comprising suitable excipients and, in some formats, inactivated viruses, subunits, or adjuvants. Dosage and ways of administration can be sorted out through normal clinical testing in so far as they are not yet available through the already registered vaccines.

Thus, the invention also provides a virus or a viral protein for use in a vaccine obtainable by a method or by a use according to the invention, the virus or the viral protein being free of any non-human mammalian proteinaceous material and a pharmaceutical formulation comprising such a virus and/or viral protein.

The invention further provides a human cell having a sequence encoding at least one E1 protein of an adenovirus or a functional derivative, homolog or fragment thereof in its genome, which cell does not produce structural adenoviral proteins and having a nucleic acid encoding a virus or at least one non-adenoviral viral protein. This cell can be used in a method according to the invention.

In a preferred embodiment, the invention provides influenza virus obtainable by a method according to the invention or by a use according to the invention. In another embodiment, the invention provides influenza vaccines obtainable by a method according to the invention or by a use according to the invention.

In another aspect, the invention provides a kit for determining activity of a protease in a sample comprising at least one viral protein or virus obtainable by a method or a use of the invention, the virus or the viral protein being free of any non-human mammalian proteinaceous material. This aspect of the invention is useful particularly for determining protease activity in culture medium. Culture medium is noted for being a difficult context for determining activity of a protease. However, by using a viral protein or a virus of the invention as a target for the protease, it is possible to accurately determine activity of the protease also in culture medium. In a preferred embodiment, therefore, the protease activity is determined in a sample comprising culture medium. In a preferred embodiment, the protease comprises trypsin. In a preferred embodiment, the viral protein comprises HA0.

In yet another aspect, the invention provides a method for concentrating influenza virus under conditions capable of, at least in part, preserving virus infectivity, comprising obtaining a cell-cleared supernatant comprising the virus from a culture of cells, and ultra-filtrating the supernatant under low shear conditions. Influenza virus preparations harvested from embryonal eggs typically need to be purified for the preparation of a vaccine. Purification typically entails at least one concentration step of the virus.

Current technologies for the concentration of influenza virus from such relatively crude preparations of influenza virus are cumbersome. Using a method of concentration of the invention, it is possible to concentrate influenza virus preparations under conditions that maintain, at least in part, infectivity of the virus. Preferably, virus is concentrated that is or can be made infectious. "Can be made infectious," as used herein, means the generation of infectious virus through cleavage of HA0.

In a preferred embodiment, the concentration is performed using a hollow fiber. A hollow fiber is particularly suited to concentrate under low shear conditions.

In a preferred embodiment, the culture of cells comprises in vitro cultured cells. Particularly suited for concentration using a method of the invention is supernatant from in vitro cultured cells, particularly when the supernatant comprises serum-free culture medium. In a preferred embodiment, the ultra-filtration is performed with a filter allowing single proteins to pass while retaining the virus. Preferably, the filter comprises a cut-off of 500 KD. More preferably, the filter comprises a cut-off of 750 KD. In a particularly preferred embodiment, the concentration further comprises at least a partial removal of proteins comprising a molecular weight smaller than 500 KD and, more preferably, smaller than 750 KD. Preferably, the purification is achieved using a mentioned filter.

In yet another aspect, the invention provides infectious influenza virus or derivatives thereof concentrated with a method of the invention. A derivative of an infectious influenza virus of the invention typically is a virus, virus particle, or viral protein or part thereof that can be used for immunization purposes. Typically, this entails a virus infectivity inactivation step.

To further illustrate the invention, the following examples are provided, which are not intended to limit the scope of the invention.

EXAMPLES

Example 1

Materials and Methods

PER.C6 and MDCK Cell Culture

MDCK cells were cultured in Dulbecco's modified Eagle's medium (DMEM, Life Technologies Breda, NL) containing 10% heat-inactivated fetal bovine serum and 1×L-Glutamine (Gibco-BRL), at 37° C. and 10% $CO_2$. Suspension cultures of PER.C6 were cultured in ExCell 525 (JRH Biosciences) supplemented with 1×L-Glutamine, at 37° C. and 10% $CO_2$, in stationary cultures in six-well dishes (Greiner) or in 490 $cm^2$ tissue culture roller bottles (Corning Costar Corp.) during continuous rotation at 1 rpm.

Immunofluorescence Test

Direct immunofluorescence assays for the detection of Influenza virus infection were carried out using the IMA-GEN™ Influenza Virus A and B kit (Dako) according to the standard protocol of the supplier. Samples were viewed microscopically using epifluorescence illumination. Infected cells were characterized by a bright apple-green fluorescence.

Propidium Iodide Staining

Cell pellets were resuspended in 300 μl of cold PBS/0.5% BSA+5 μl of propidium iodide (concentration 50 μg/ml) in PBS/FCS/azide solution known to persons skilled in the art. Viable and dead cells were then detected via flow cytofluorometric analysis.

Hemagglutination Assay

In general, hemagglutination assays for Influenza virus titers were performed according to methods known to persons skilled in the art. Here, 50 μl of a two-fold diluted virus solution in PBS was added to 25 μl PBS and 25 μl of a 1% suspension of turkey erythrocytes (Biotrading Benelux B.V.) in PBS and incubated in 96-well microtiter plates at 4° C. for one hour. The hemagglutination pattern was examined and scored and expressed as hemagglutinating units (HAUs). The number of HAUs corresponded to the reciprocal value of the highest virus dilution that showed complete hemagglutination.

Western Blot Analysis of the Influenza HA Protein

In general, obtained influenza viruses were disrupted in a Laemmli buffer according to methods known in the art and different volumes of obtained protein mixtures were separated using 10% SDS/PAGE gels. In brief, blots were blocked for 30 minutes at room temperature with block solution (5% nonfat dry milk powder (Biorad) in TBST supplemented with 1% rabbit serum (Rockland), followed by three washes with TBST. Then, the blots were incubated with the anti-A/Sydney/5/97 HA antiserum (98/768 NIBSC) diluted 1/500 in 1% BSA/TBST with 5% rabbit serum (Rockland) O/N at room temperature. Again, the blots were washed eight times with TBST. Finally, the blots were incubated with the rabbit anti-sheep antiserum (HRP-labeled, Rockland) 1/6000 diluted in block solution for one hour at room temperature. After eight washes with TBST, the protein-conjugate complex was visualized with ECL (Amersham Pharmacia Biotech), and films (Hyperfilm, Amersham Life Science) were exposed. The antisera were obtained from the NIBSC (UK) and applied in dilutions recommended by the NIBSC.

Single Radial Immunodiffusion (SRID) Assay

The concentration of hemagglutinin in supernatants, derived from influenza virus infected-PER.C6 cells, was determined by the single radial immunodiffusion (SRID) test as previously described (Wood et al. 1977). The assay was performed using standard NIBSC (UK) antigens and antisera reagents.

Plaque Assay

A total of 1 ml of ten-fold serially diluted viral supernatants were inoculated on MDCK cells which were grown until 95% confluence in six-well plates. After one hour at 35° C., the cells were washed twice with PBS and overloaded with 3 ml of agarose mix (1.2 ml 2.5% agarose, 1.5 ml 2×MEM, 30 ml 200 mM L-Glutamine, 24 ml trypsin-EDTA, 250 ml PBS). The cells were then incubated in a humid, 10% $CO_2$ atmosphere at 35° C. for approximately three days and viral plaques were visually scored.

Virus Infectivity Assay ($TCID_{50}$)

Titration of infectious virus was performed on MDCK cells. In brief, cells were seeded in 96-well plates at a density of $4 \times 10^4$ cells/well in DMEM supplemented with 2 mM L-Glutamine. Twenty-four hours later, cells were infected with 100 μl of ten-fold serially diluted culture supernatants, in quadruplicate, in medium containing Trypsin-EDTA at the concentration of 4 mg/ml. Two hours after infection, cell monolayers were washed two times in PBS and incubated in medium containing trypsin for seven days at 35° C. Supernatants from these cultures were then tested in an HA assay. $TCID_{50}$ titers were calculated according to the method of Karber (1931).

b-propiolactone Influenza Virus Inactivation

For inactivation of the viruses to obtain whole-inactivated virus for the generation of vaccines derived from PER.C6, a mutation protocol known to persons skilled in the art was performed using b-propiolactone. b-propiolactone is a very effective agent widely used for the inactivation of viruses and well known in the art for its mutating effects. It modifies nucleic acid bases of the viral genome and the host cell genome and blocks replication thereafter. Following an established protocol used to prepare the whole inactivated influenza vaccine prepared on embryonated eggs, the amount of virus corresponding to approximately 400 mg of HA per strain was inactivated and used for the final vaccine formulation. Briefly, one volume of 0.3 M sodium phosphate buffer was added to nine volumes of influenza virus preparation. Inactivation of the viruses was carried out adding one volume of 10% of b-propiolactone (Newall Design, UK) to 100 volumes of phosphate-buffered virus preparation and incubated at 20° C. for 24 hours. Inactivation of the viruses was checked by plaque assay and no plaques were detected for any of the inactivated batches (data not shown).

Example 2A

PER.C6 Cell Banking and Pre-culture

Cell line PER.C6, or derivatives thereof, were used. Cell lines were banked by a two-tier cell bank system. The selected cell line was banked in a research master cell bank (rMCB) which was stored in different locations. From this rMCB research, working cell banks (rWCB) were prepared as follows: an ampoule of the rMCB was thawed and cells were propagated until enough cells are present to freeze the cells by using dry ice. Up to 500 ampoules containing 1 ml ($1$-$2\times10^6$ cells/ml) of rWCB were stored in the vapor phase of a liquid $N_2$ freezer.

One ampoule containing $5\times10^6$ PER.C6 cells of the WCB was thawed in a water bath at 37° C. Cells were rapidly transferred into a 50 ml tube and resuspended by adding 9 ml of the suspension medium ExCell 525 (JRH Biosciences) supplemented with 1×L-Glutamine. After three minutes of centrifugation at 1000 rpm in a tabletop centrifuge, cells were resuspended in a final concentration of $3\times10^5$ cells/ml and cultured in a T80 tissue culture flask at 37° C. 10% $CO_2$. Two to three days later, cells were seeded into 490 $cm^2$ tissue culture roller bottles (Corning Costar Corp.), with a density of $3\times10^5$ per ml and cultured in continuous rotation at 1 rpm.

Example 2B

PER.C6 Cells as Permissive Cell Line for Influenza A Virus

PER.C6 as a human cell was not known for its ability to sustain influenza virus infection and replication. It was, therefore, determined whether PER.C6 cells are permissive for influenza virus infection in comparison with the dog cell line MDCK that served as a positive control.

On the day before infection, $2\times10^5$ MDCK cells per well were seeded in six-well plates. Twenty-four hours later, $4\times10^5$ seeded PER.C6 and the MDCK cells per well were infected with the H1N1 strain A/Puerto Rico/8/34 (titer 3.6× $10^7$ pfu/ml) (obtained from Dr. E. Claas, Leiden University Medical Center, The Netherlands). Infection was performed at various multipliticies of infection (mois) ranging from of 0.1 to 10 pfu/cell. After about two hours of incubation at 37° C., the inoculum was removed and replaced by fresh culture medium. A direct immunofluorescence assay for the detection of influenza virus infection was performed 24 and 48 hours post-infection. The experiment showed permissiveness of PER.C6 for influenza infection, with percentages of positive cells moi-dependent and comparable with MDCK (FIG. 1).

Example 3

PER.C6 Used for Influenza A Virus Propagation

It was verified whether replication and propagation of influenza virus could be supported by PER.C6. On the day of infection, PER.C6 cells were seeded in 490 $cm^2$ tissue culture roller bottles with the density of $2\times10^5$ cells/ml in a final volume of 40 ml in the presence of 5 μg/ml of trypsin-EDTA (Gibco-BRL). Cells were either mock inoculated or infected with the H3N2 strain A/Shenzhen/227/95 (titer $1.5\times10^6$ pfu/ml) (obtained from Dr. E. Claas, Leiden University Medical Centre, The Netherlands). Infections were performed at moi $10^{-4}$ and $10^{-3}$ pfu/cell. After one hour of incubation at 37° C., the inoculum was removed by spinning down the cells at 1500 rpm and resuspending the cells in fresh culture medium +5 μg/ml of trypsin-EDTA. Harvest of 1.3 ml of cell suspension was carried out each day, from day 1 to day 6 post-infection. Supernatants were stored at −80° C. and used for hemagglutination assays. Cell pellets were used for direct immunofluorescence tests and for propidium iodide staining.

Example 4

Permissiveness of PER.C6 for Different Influenza Strains

Figure 4:
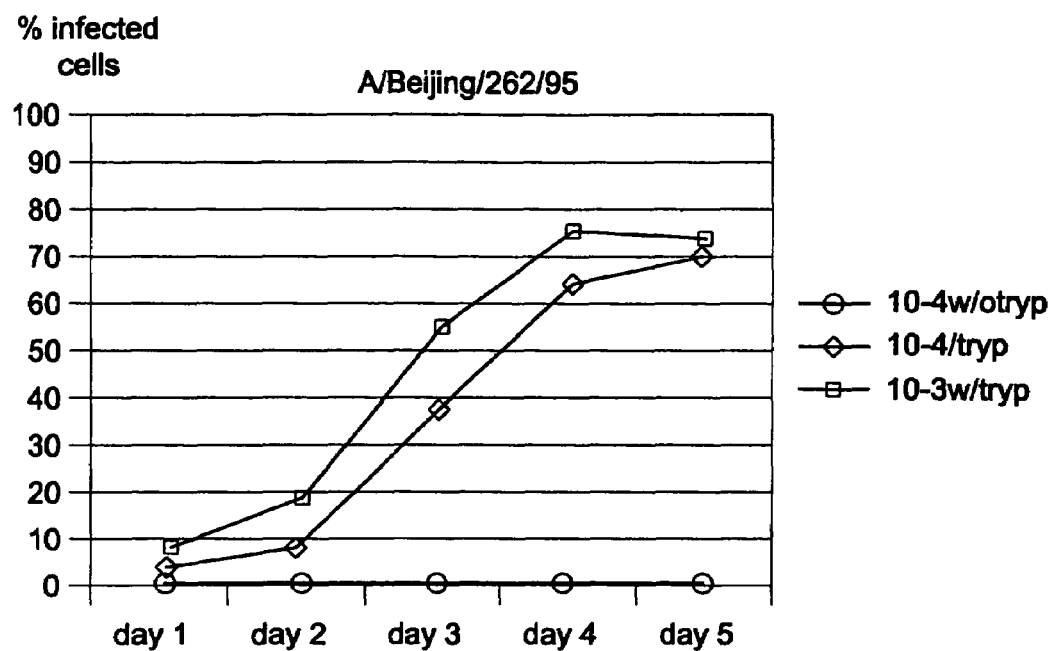
FIG. 4 consists of two graphs depicting percentage of infected cells (positive cells) viewed microscopically after immunofluorescence assay.
Figure 4:
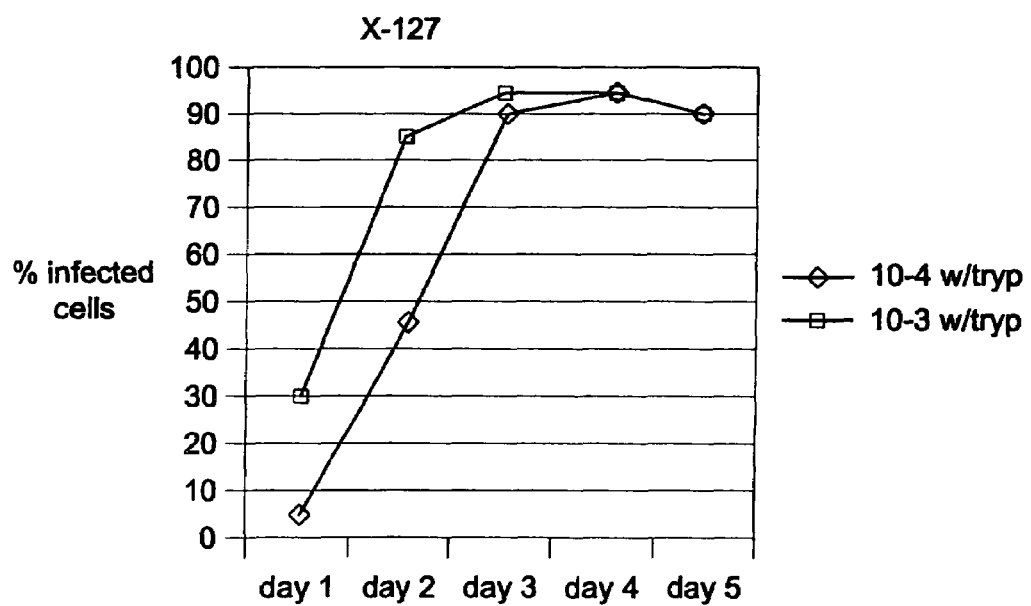
Figure 5:
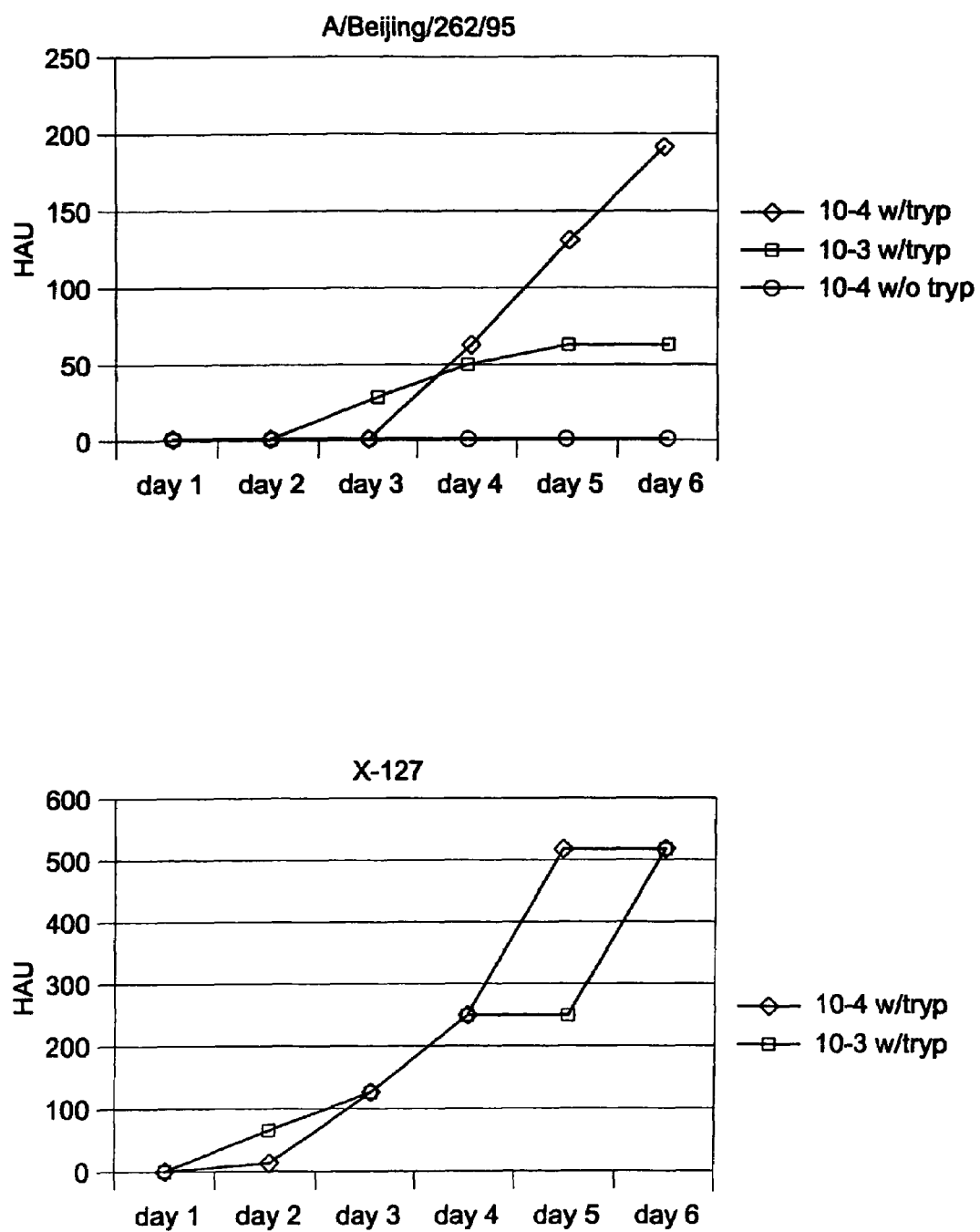
FIG. 5 consists of two graphs depicting kinetics of virus propagation measured in HAU from day 1 through day 6 after infection.

To further investigate the permissiveness of PER.C6 for propagation of various influenza strains, an infection by using the H1N1 vaccine strains A/Beijing/262/95 and its reassortant X-127, obtained from the National Institute for Biological Standards and Control (NIBSC, UK), was performed. On the day of infection, PER.C6 cells were seeded in 490 $cm^2$ tissue culture roller bottles with the density of approximately $1\times10^6$ cells/ml in a final volume of 50 ml. Cells were inoculated with 5 μl ($10^{-4}$ dilution) and 50 μl ($10^{-3}$ dilution) of virus in the presence of 5 mg/ml trypsin-EDTA. In order to establish if trypsin was indeed required, one more infection was carried out by inoculating 5 μl of the strain A/Beijing/262/95 in the absence of the protease. After approximately one hour of incubation at 37° C., the inoculum was removed by spinning down the cells at 1500 rpm and resuspending them in fresh culture medium ±5 mg/ml of trypsin-EDTA. At day 2 and day 4 post-infection, more trypsin was added to the samples. Harvest of 1.3 ml of cell suspension was carried out from day 1 to day 6 post-infection. Supernatants were stored at −80° C. and used for hemagglutination assays and further infections; cell pellets were used for direct immunofluorescence tests. Results obtained with the above-mentioned immunofluorescence and hemagglutination assays are shown in FIGS. 4 and 5, respectively, illustrating the efficient replication and release of the viruses.

Example 5

Infectivity of Virus Propagated on PER.C6

Figure 6:
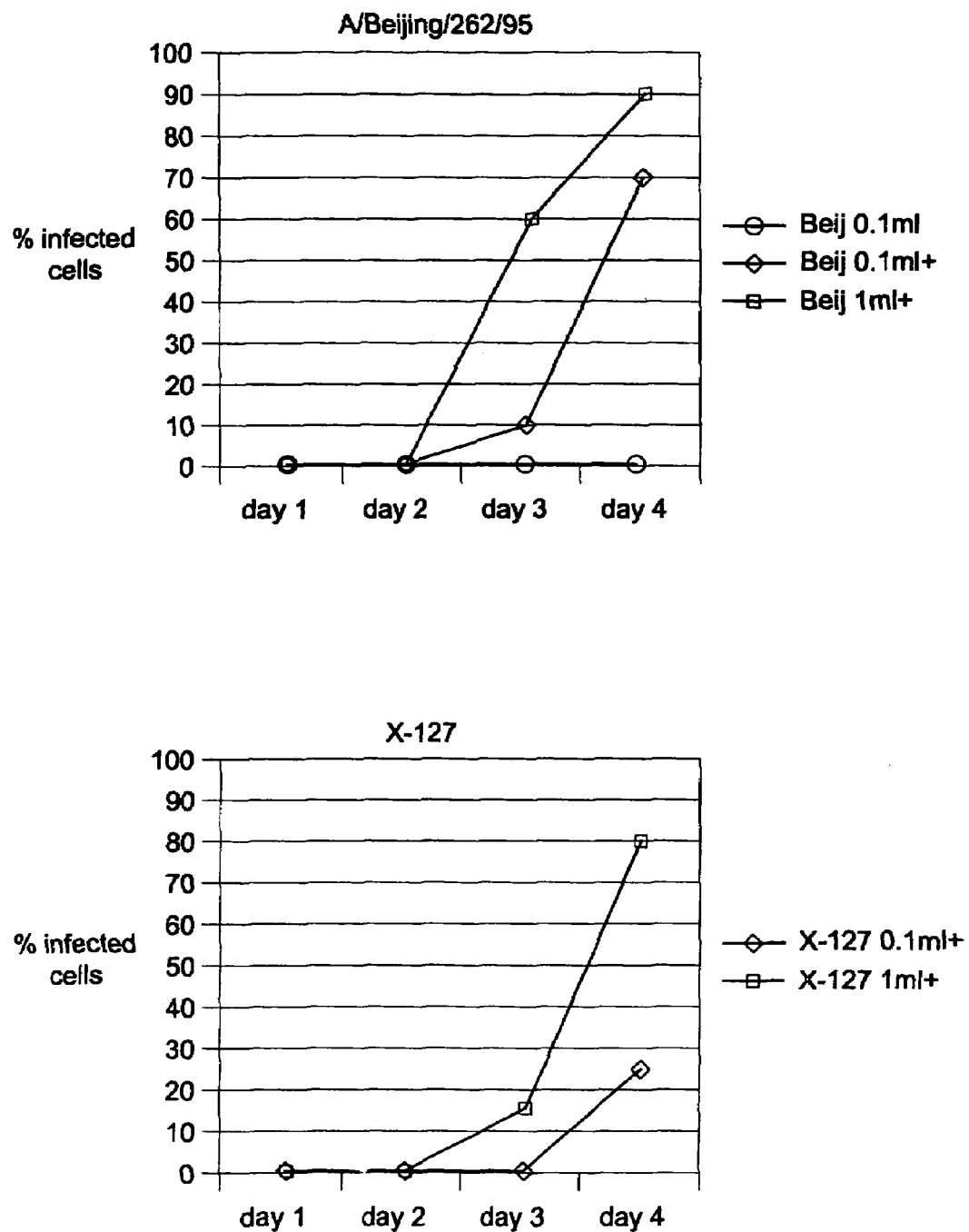
FIG. 6 consists of two graphs depicting percentage of infected cells (positive cells) viewed microscopically after immunofluorescence assay.
Figure 7:
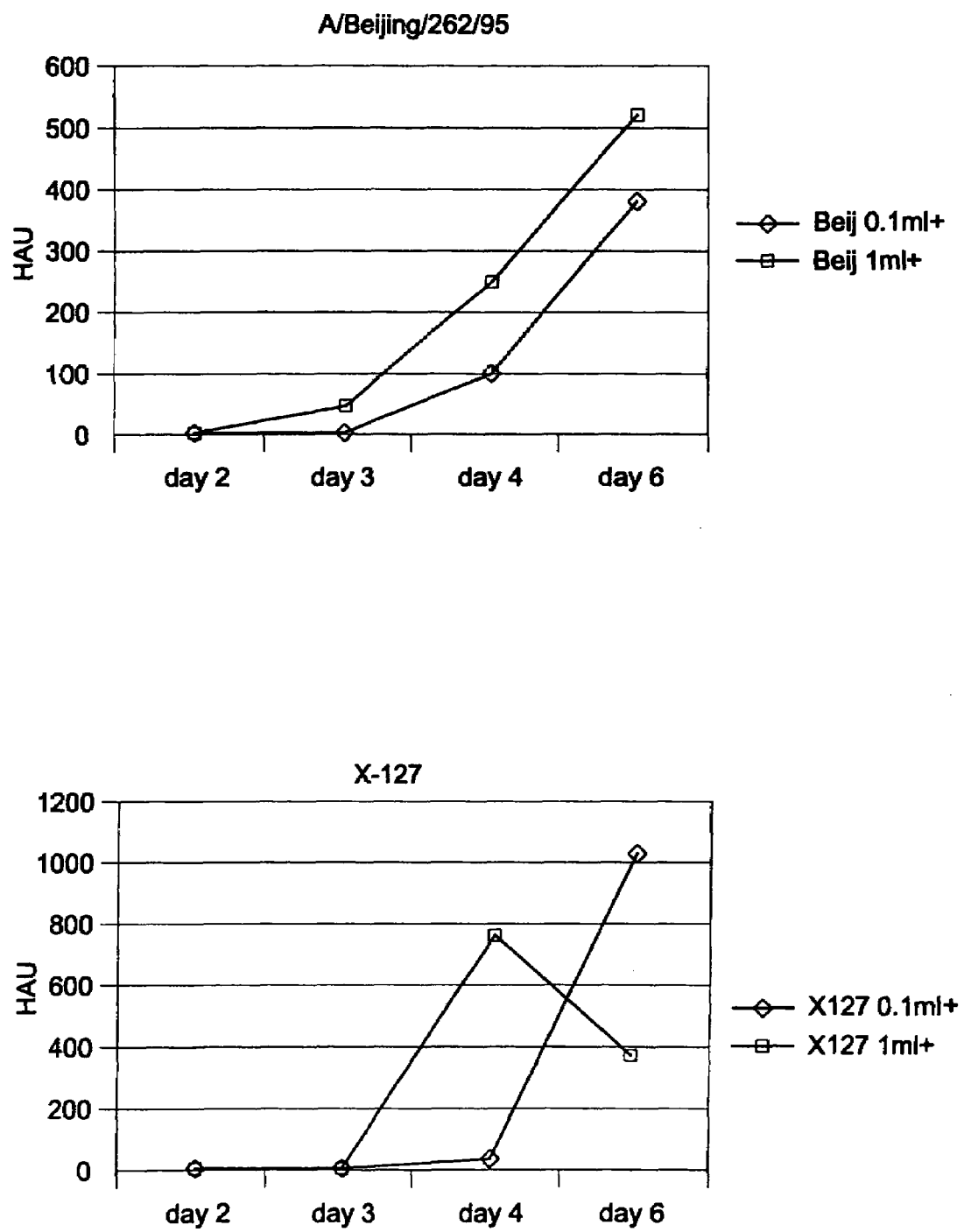
FIG. 7 consists of two graphs depicting kinetics of virus propagation measured in HAU from day 2 through day 6 after infection.

It was verified whether the viruses grown in PER.C6 were infectious and if adaptation to the cell line could increase virus yields. Virus supernatants derived from PER.C6 infected with the strains A/Beijing/262/95 and its reassortant X-127 (dil.10-3) and harvested at day 6 post-infection were used. At the day of infection, PER.C6 were seeded in 490 $cm^2$ tissue culture roller bottles, with the density of approximately $1\times10^6$ cells/ml in a final volume of 50 ml. Cells were inoculated with 100 μl and 1 ml of virus supernatant in the presence of 5 mg/ml trypsin-EDTA. In order to establish if trypsin was still required, one more infection was carried out by inoculating 100 μl of the strain A/Beijing/262/95 in the absence of the protease. After approximately one hour of incubation at 37° C., the inoculum was removed by spinning down the cells at 1500 rpm and resuspending them in fresh culture medium ±5 mg/ml of trypsin-EDTA. At day 2 and day 4 post-infection, more trypsin was added to the samples. Harvest of 1.3 ml of cell suspension was carried out from day 1 to day 6 post-infection. Supernatants were stored at −80° C. and used for hemagglutination assays and further infections; cell pellets were used for direct immunofluorescence tests. Results obtained with the above-mentioned immunofluorescence and hemagglutination assays are shown in FIGS. 6 and 7. Data obtained with the present experiment showed infectivity of the viruses grown in PER.C6 as well as an increase in virus yields.

Example 6

The Presence of Cell Surface Receptors for Influenza Virus on PER.C6

Figure 8:
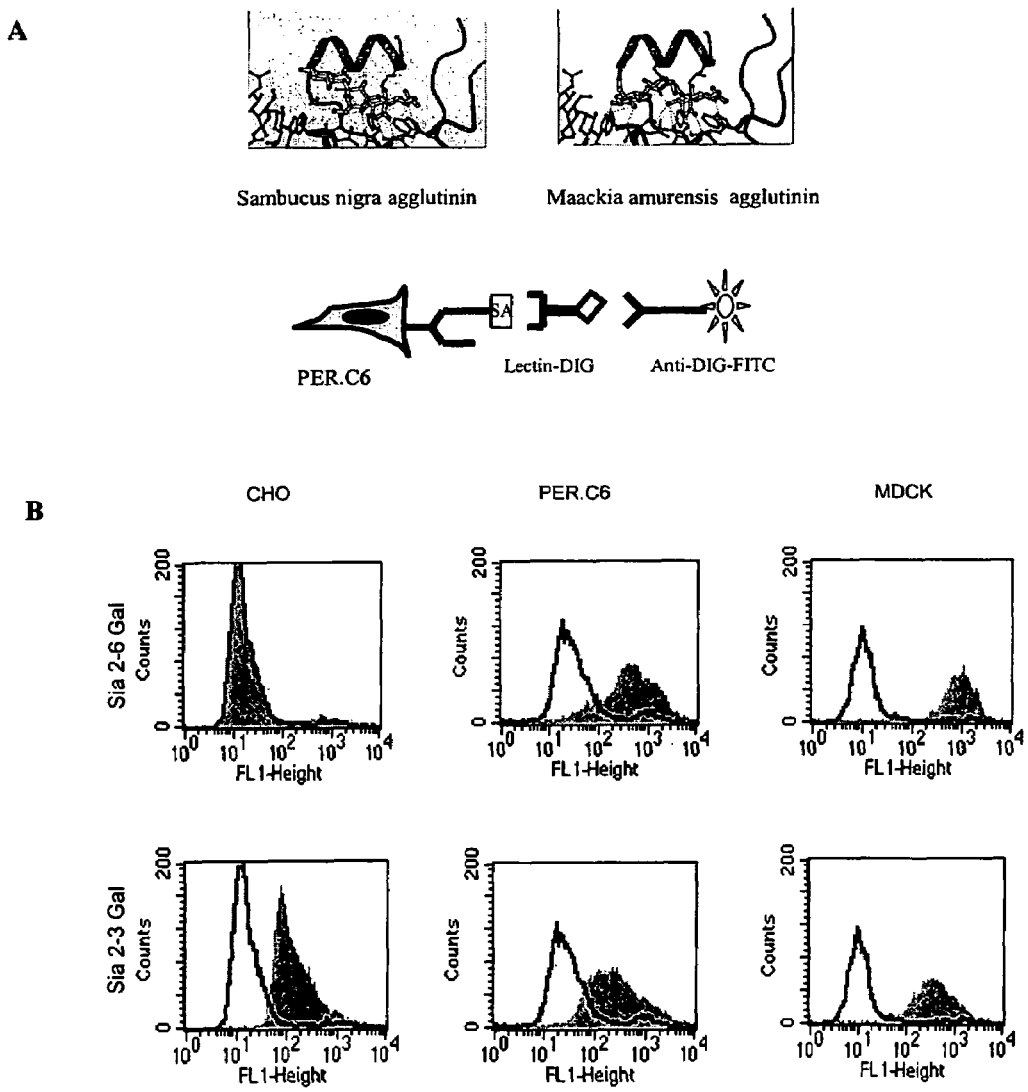
FIG. 8 consists of portions A and B depicting expression of Sia2-3Gal and Sia2-6Gal linkages on cell surface receptors present on Chinese Hamster Ovary (CHO) cells, PER.C6 cells and MDCK cells. Portion A is a schematic representation of the interaction of the Sambucus nigra agglutinin (SNA) lectin that specifically recognizes Sia2-6Gal linkages and the Maackia amurensis agglutinin (MAA) lectin that specifically recognizes Sia2-3Gal linkages. The schematic interaction with the FITC-labeled anti-DIG antibody recognizing the DIG-labeled lectin bound to the oligosaccharide chain on the cell surface protein is also depicted. Portion B depicts FACS analysis of cells incubated with DIG-labeled lectins. Lectins attached to the cells were detected with FITC-labeled anti-DIG antibody using procedures known to persons skilled in the art. Cell number counts are plotted against the fluorescence intensity of lectin-stained cells (gray) as compared with cells that were incubated only with the FITC-anti-DIG antibody (open). The upper panels of Portion B show the shift in the FACS analysis obtained by using the SNA lectin, while the lower panels of Portion B show the shift in the FACS analysis obtained by using the MAA lectin.

Propagation of human Influenza A and B strains in embryonated chicken eggs leads to a selection of receptor-binding variants that harbor amino acid substitutions at the distal portion of the HA globular head in the exposed and functionally important regions of the molecule. Because of these mutations, the egg-adapted strains can differ from the original human viruses in their antigenic and immunogenic activities, as well as their virulence. Human influenza viruses isolated from MDCK cells usually present an HA protein that is identical to the HA protein present on the virus of the original clinical sample. A recent study (Govorkova 1999) clarified the molecular basis for the selection of variants in chicken eggs and the absence of this variant selection phenomenon in MDCK cells. All human Influenza A and B strains isolated from MDCK cells were found to bind with high affinity and specificity for alpha2,6 sialic acid-galactose linkages present in oligosaccharides present in cell surface receptors, whereas their egg-grown counterparts showed an increased affinity for the alpha2,3 sialic acid-galactose linkages in cell surface receptors carrying oligosaccharides (Sia2-3Gal). Using specific lectins, it was demonstrated that only Sia2-3Gal-containing receptors were present on the surface of chicken embryonic cells, whereas MDCK cells expressed both Sia2-6Gal and Sia2-3Gal. The expression of the Sia2-3Gal and Sia2-6Gal moieties on the surface of PER.C6 cells was studied by FACS analysis, using two different digoxigenin-(DIG-) labeled lectins: Sambuca nigra agglutinin (SNA) that specifically recognizes Sia2-6Gal linkages and the Maackia amurensis agglutinin (MAA), that specifically recognizes Sia2-3Gal linkages. FIG. 8A shows the recognition of the SNA and MAA lectins and their binding to the glycosylation sites. Furthermore, FIG. 8A shows the schematic interaction between the FITC-labeled anti-DIG antibody and the DIG-labeled lectin that recognizes the specific sialyl bond in the glycosylation backbone of the receptor present on the cell surface. Both lectins were taken from the glycan differentiation kit (Boehringer-La Roche).

The experiment was carried out on PER.C6 cells in suspension and adherent MDCK and CHO cells. MDCK and CHO cells were released from the solid support using trypsin-EDTA (Gibco-BRL). The cell suspensions were then washed once with Mem-5% FBS and incubated in this medium for one hour at 37° C. After washing with PBS (Gibco-BRL), the cells were resuspended to a concentration of approximately $10^6$ cells/ml in binding medium (Tris-buffered saline, pH 7.5, 0.5% BSA, and 1 mM each of $MgCl_2$, $MnCl_2$ and $CaCl_2$). Cell aliquots were incubated for one hour at room temperature with the DIG-labeled lectins SNA and MAA. After one hour, lectin-treated cells were washed with PBS and incubated for an additional hour at room temperature with FITC-labeled anti-DIG antibody (Boehringer-Mannheim). Finally, the cells were washed with PBS and analyzed by fluorescence-activated cell sorting using a FAC-sort apparatus (Becton Dickinson). The results shown in FIG. 8B demonstrate that PER.C6 cells were stained by both lectins showing the presence of the Sia2-6Gal as well as the Sia2-3Gal receptors.

In the same experiment, MDCK cells were used as positive control for both the sialylated receptors, whereas CHO cells, due to the absence of the alpha 2-6 sialyltransferase glycosylation enzyme in these hamster cells, represented a negative control for the Sia2-6Gal moiety. The upper panels show results with the SNA lectin and the lower panels showing results with the MAA lectin. From these results, it can be concluded that PER.C6 expresses cell surface proteins that have both Sia2-3Gal and Sia2-6Gal linkages in their oligosaccharide chains.

Example 7

Effect of Different Concentrations of Trypsin-EDTA on the Viability of PER.C6 Cells, on the Influenza Virus Production in PER.C6 Cells and on the Ha Protein Derived Thereof Due to the absolute trypsin requirement for the propagation of influenza viruses in cell cultures, the effects of different concentrations of trypsin-EDTA on PER.C6 cell viability and virus replication in PER.C6 cells after infection using several Influenza strains were investigated.

Infection with Influenza Virus Strain A/Sydney/5/97 in the Presence of Low Concentrations of Trypsin On the day of infection, PER.C6 cells were seeded in 490 $cm^2$ tissue culture roller bottles at a density of $1 \times 10^6$ cells/ml in the presence of trypsin-EDTA at final concentrations of 0.5, 1, 2, 3 and 5 mg/ml.

Figure 9:
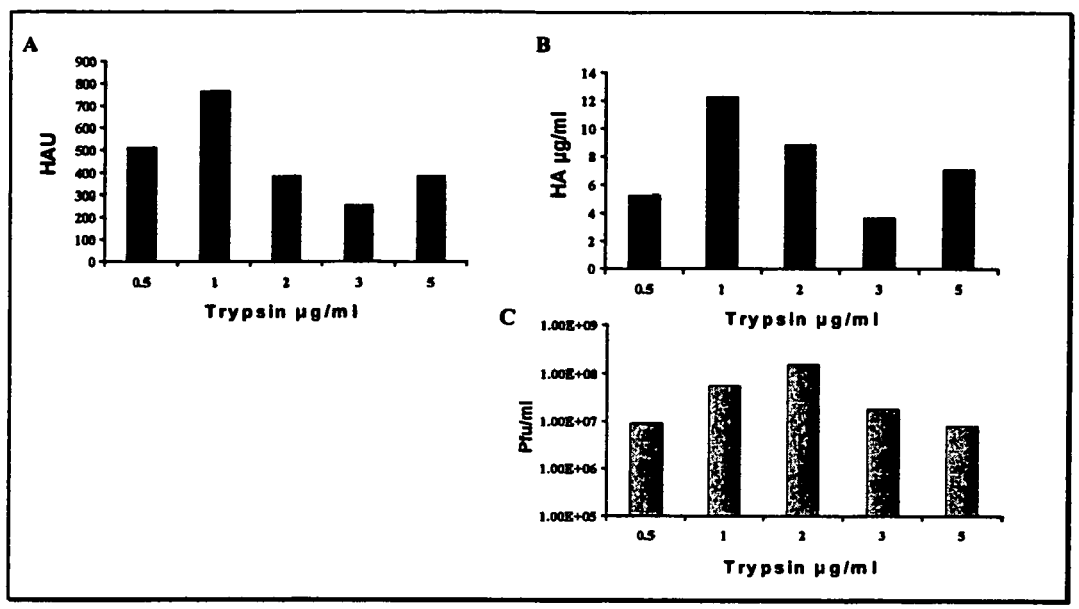
FIG. 9 consists of Portions A, B, and C, depicting infection with A/Sydney/5/97 on PER.C6. (A) Effect of trypsin-EDTA on HAU titers. (B) HA concentration in µg/ml and (C) virus infectivity titers in pfu/ml as measured in crude viral supernatants, 96 hours post-infection.

These trypsin concentrations did not interfere with the growth characteristics of the cells and their viability (data not shown). Cells were either mock infected or infected with PER.C6-grown Influenza virus A/Sydney/5/97 at an moi of $10^{-4}$ pfu/cell. The viral production was monitored by direct immunofluorescence (data not shown), hemagglutination assays, single-radial-immunodiffusion (SRID) above and plaque assays, all as described above. Results from this experiment are depicted in FIG. 9 and show that the HA content as measured by SRID, as well as the biological activity of the virus expressed in HAU, were highest when a trypsin concentration of 1 mg/ml was used. FIG. 9 also shows that by using a plaque assay the highest number of plaque forming units (pfu) per ml was observed in the sample corresponding to cells grown in medium containing 2 mg/ml of trypsin.

Infection with Influenza Virus Strain B/Harbin/7/94

Figure 10:
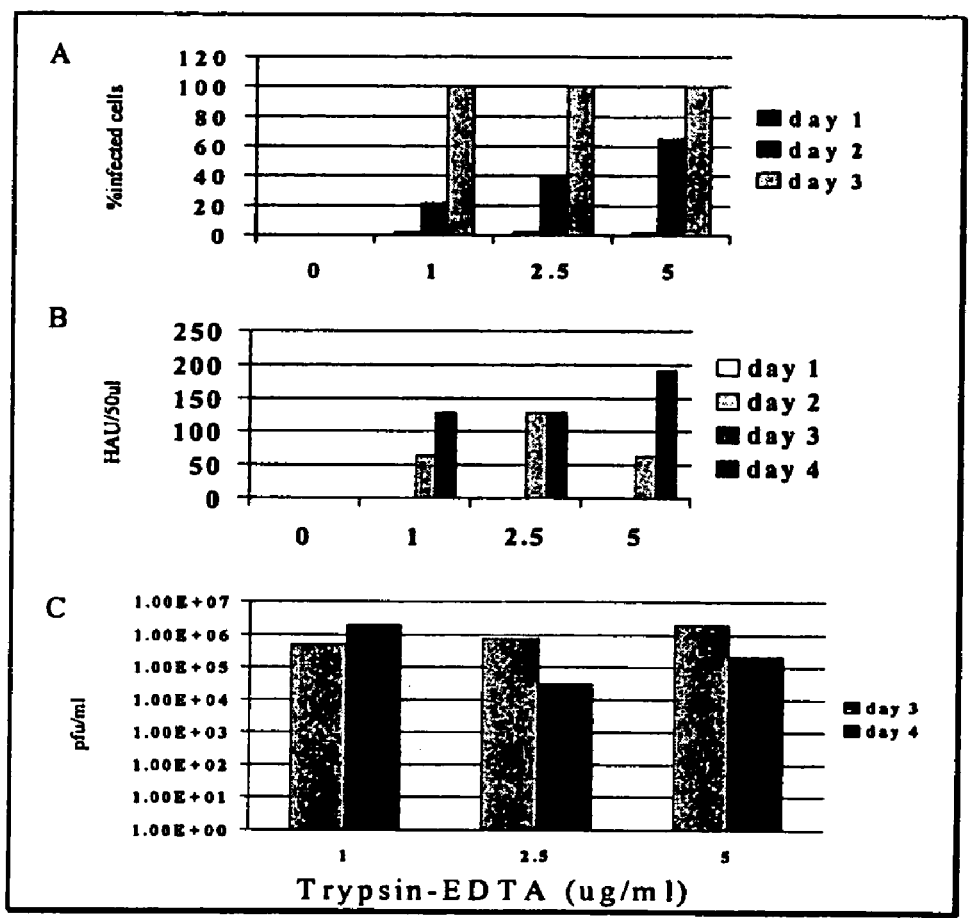
FIG. 10 consists of Portions A, B, and C depicting infection with B/Harbin/7/94 on PER.C6. (A) Effect of different concentrations of trypsin-EDTA present during and after virus infection on growth kinetics. (B) HAU titers per 50 µl and (C) virus infectivity titers in pfu/ml.

On the day of infection, PER.C6 cells were seeded in 490 $cm^2$ tissue culture roller bottles at a density of $1 \times 10^6$ cells/ml in the presence of different concentrations of trypsin-EDTA ranging from 1 to 5 mg/ml. Cells were infected with PER.C6-grown virus B/Harbin/7/94 at an moi of $10^{-3}$ pfu/cell. Production of the virus was monitored by direct immunofluorescence, hemagglutination and plaque assays as shown in FIG. 10. The infectability of PER.C6 at day 2 increased with the concentration of trypsin. At day 3, however, no significant difference was observed in the percentage of infected cells when 1, 2.5 or 5 mg/ml trypsin was present. In the absence of trypsin (0 μg/ml), no influenza virus infection was detected. At the day of the last harvest (day 4 post-infection), the biological activity of the virus, as measured by hemagglutination assay, did not differ significantly. Interestingly, the infectivity assay performed in samples that were taken at days 3 and 4 after infection showed a difference in the production of the virus. The highest titers were obtained at day 3 and day 4 when a trypsin concentration of 2.5 to 5 (day 3) and 1 mg/ml (day 4) were used.

Infection with Influenza Virus Reassortant X-127

Figure 11:
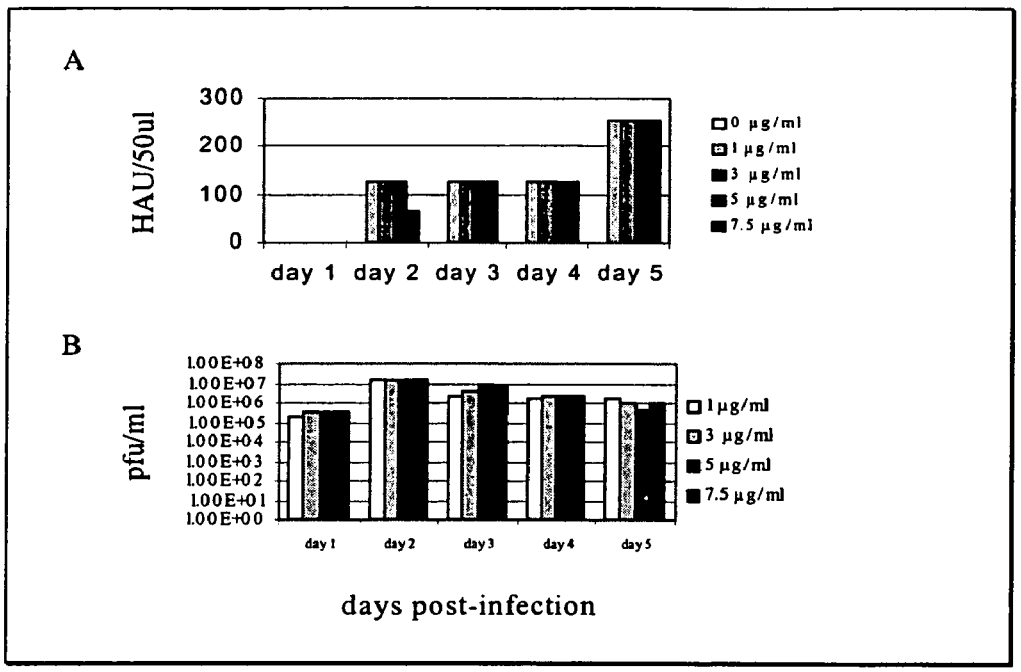
FIG. 11 consists of Portions A and B which depict infection with X-127 using an moi of $10^{-3}$ on PER.C6. (A) Effect of trypsin-EDTA on HAU given in HAU/50 µl and (B) virus infectivity titers in pfu/ml for five days after infection.
Figure 12:
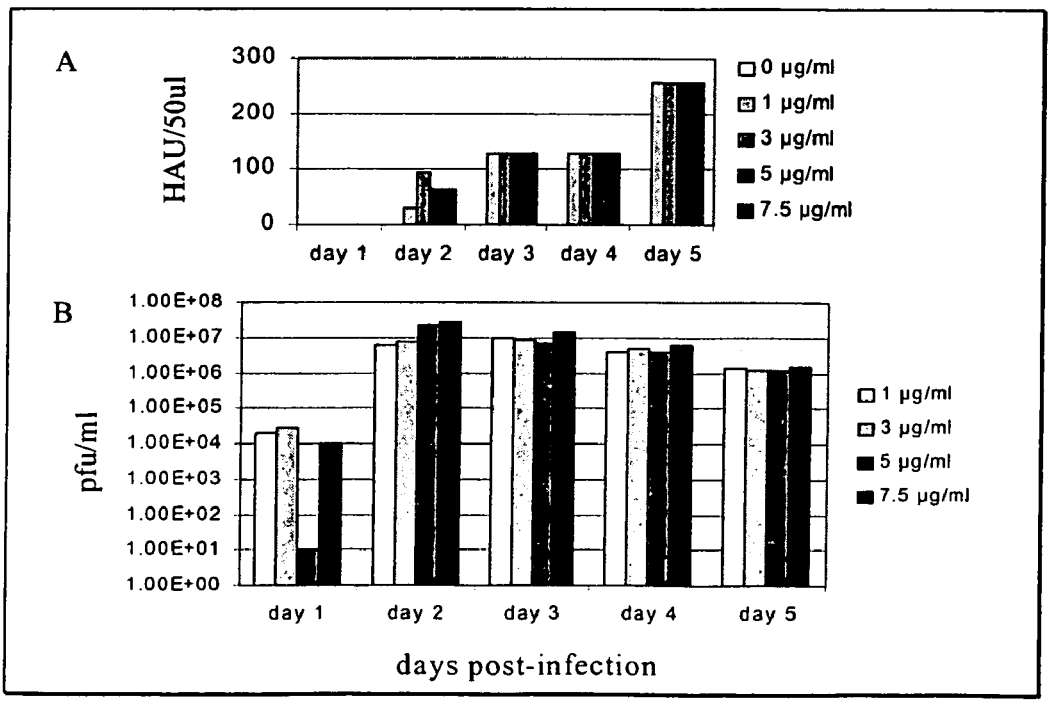
FIG. 12 consists of Portions A and B depicting infection with X-127 using an moi of $10^{-4}$ on PER.C6. (A) Effect of trypsin-EDTA on HAU given in HAU/50 µl and (B) virus infectivity titers in pfu/ml during five days after infection.

On the day of infection, PER.C6 cells were seeded in T25 tissue culture flasks at a density of $1 \times 10^6$ cells/ml in the presence of different concentrations of trypsin-EDTA ranging from 0 to 7.5 mg/ml. Cells were infected with PER.C6-grown virus X-127 (egg-reassortant for the strain A/Beijing/262/95) at an moi of $10^{-4}$ and $10^{-3}$ pfu/cell. Viral growth was monitored by direct immunofluorescence, hemagglutination and plaque assays. As shown in FIG. 11 and FIG. 12, HAU titers were identical between samples, independent of the trypsin concentration and the initial moi that was used. Furthermore, no significant differences were observed in the infectivity titers as measured by plaque assay.

Infection of PER.C6 with Influenza Virus Strain A/Sydney/5/97 in the Presence of High Concentrations of Trypsin To test the effect of increasing concentrations of trypsin on viability of the cells and virus replication, PER.C6 cells were seeded in roller bottles at a density of $1 \times 10^6$ cells/ml in the presence of various concentrations of trypsin-EDTA ranging from 0 to 12.5 μg/ml. Cells were either mock infected or infected with PER.C6-grown virus A/Sydney/5/97 virus at an moi of $4 \times 10^{-5}$ pfu/cell. HAU's presence in the obtained batches were determined as described. Importantly, data depicted in FIG. 13 clearly show that trypsin concentrations up to 10 μg/ml do not interfere with the cell viability. Moreover, the biological activity of the virus obtained at day 4 after infection as measured by HAU was higher when a trypsin concentration of 2.5 to 5 μg/ml was used. Furthermore, the $TCID_{50}$ was measured (FIG. 14, graph portion A) and plaque assays were performed (data not shown). No relevant differences were found in these plaque assays, in the infectivity titers ($TCID_{50}$), in the HA cleavage and quantity (approximately 10 μg/ml) as determined by western blot analysis shown in FIG. 14B.

Example 8

Influenza Virus Production on PER.C6 Cells in a Hollow Fiber-Perfusion Bioreactor System The scalability of influenza virus production in suspension growing PER.C6 cells was studied by using 3-liter (total volume) bioreactors containing a 2 liter cell suspension volume in serum-free medium, which is also free of animal- or human-derived proteins (ExCell 525, JRH Biosciences).

Influenza infection was carried out at a cell density of approximately $3 \times 10^6$ cells/ml. Cells were inoculated with PER.C6-grown A/Sydney/5/97 virus, at an moi of $10^{-4}$ pfu/cell. Samples of 5 to 10 ml of cell suspensions were taken every day to perform general cell counts, to determine the viability of the cells, for glucose concentration measurements, for direct immunofluorescence, for hemagglutination and for infectivity assays. The results of these experiments are shown in FIG. 15.

To investigate the presence and the status of the HA protein western blots using two different anti-HA antibodies obtained from NIBSC were used. SRID assays as described above were also performed. The results depicted in the two western blots in FIG. 16 show that the Influenza virus batch produced in this bioreactor yielded an HA content of an estimated concentration of 15 μg/ml which was confirmed by SRID assays. The HA produced is comparable to reference NIBSC HA in terms of subunit composition and immune reactivity with the reference subtype-specific antis era.

Example 9

Infection of PER.C6 with A/Sydney/5/97 in a 15 Liter Bioreactor Followed by a specific Down Stream Process (DSP)

Suspension growing PER.C6 cells was incubated at 37° C. in a 15-liter bioreactor hollow fiber perfusion system, with a cell suspension volume of 10 liters in serum-free ExCell 525 medium (JRH Biosciences). Influenza infection was carried out at 35° C. at a cellular density of approximately $3.3 \times 10^6$ cells/ml in medium containing 5 mg/ml trypsin-EDTA (Life Technologies). Cells were inoculated with PER.C6-grown A/Sydney/5/97 virus (passage number 3) at an moi of $10^{-4}$ pfu/cell. Perfusion with serum-free ExCell 525 medium containing trypsin-EDTA was continued during the first 24 hours upon infection. Two days post-infection, cells were fed with a fed-batch solution containing glucose, essential amino acids and extra glutamine: 82 ml per liter suspension containing 50 m/v % glucose (NPBI-The Netherlands), 50× essential amino acids without Gln (Gibco-BRL-Life Technologies) and 200 mM glutamine (Gibco-BRL-Life Technologies). Cell suspension samples of 10 ml were taken every day in order to perform standard cell counts (results shown in FIG. 17, left graph), glucose concentration measurements (results shown in FIG. 17, right graph), direct immunofluorescence (FIG. 18), hemagglutination (FIG. 19) and infectivity assays (data not shown). Furthermore, the HA protein was investigated by western blot analysis and compared to an NIBSC standard HA control (FIG. 20). On the day of the final harvest of the entire cell suspension (92 hours post-infection), a cell debris clarification was performed in a continuous flow at 20,000 g using the Powerfuge™ separation system (Carr, JM Separations) according to the protocols provided by the manufacturer. Clarified supernatant was then concentrated twentyfold using a hollow fiber membrane cartridge of 500 kD cut-off (A/G Technology, JM Separations). The results depicted in FIG. 21 show that the quantitative recovery of live influenza virus after concentration by hollow fiber as measured by hemagglutination and infectivity assays is very significant.

Example 10

The Immunogenicity of PER.C6-Grown Influenza Viruses and Vaccines Derived Therefrom To determine the immunogenicity of PER.C6-grown influenza viruses, an in vivo study and challenging model in ferrets was designed. Two batches of trivalent whole-inactivated influenza vaccine (composed of A/Sydney/5/97, A/Beijing/262/95 and B/Harbin/7/94), containing 15 μg HA of each of the three strains, were used. The first batch was obtained from fertile hens' eggs and the second was obtained from PER.C6 cells. Production, purification, inactivation and formulation of the trivalent whole-inactivated PER.C6-derived Influenza vaccines were performed as described below.

Growth of A/Sydney/5/97, A/Beijing/262/95 and B/Harbin/7/94 Influenza strains on PER.C6

Figure 22:
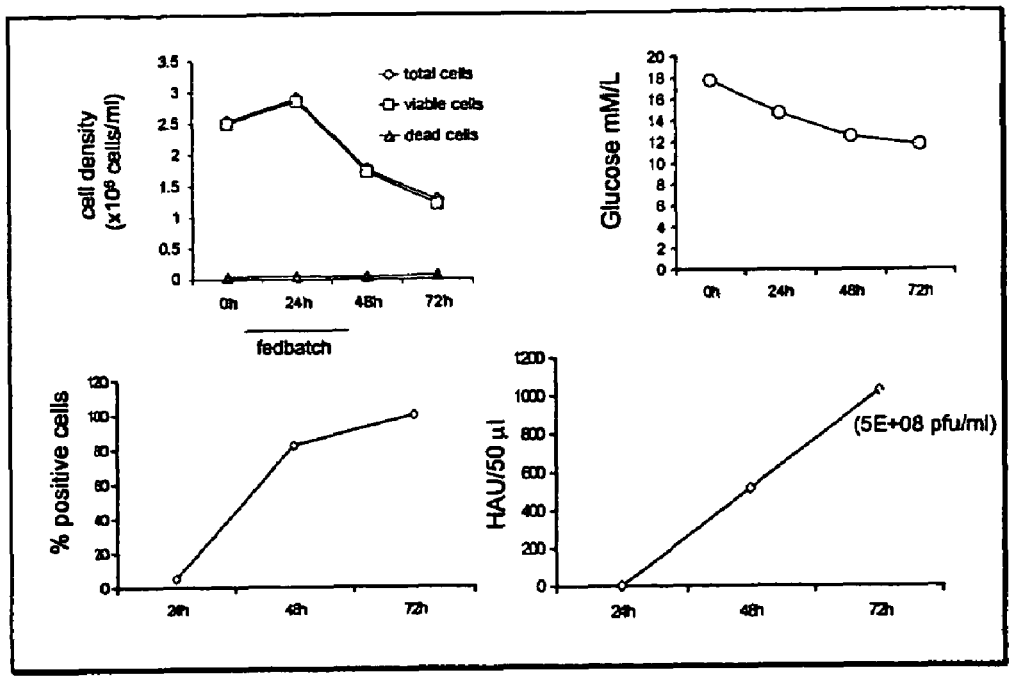
FIG. 22 consists of four graphs depicting infection of PER.C6 with A/Sydney/5/97 in a 2 liter cell suspension in a 3 liter bioreactor. PER.C6 cells viability (upper left), glucose concentration (upper right) and growth kinetics of the virus in the percentage of positively staining cells (lower left), and HAUs (lower right) are given.
Figure 23:
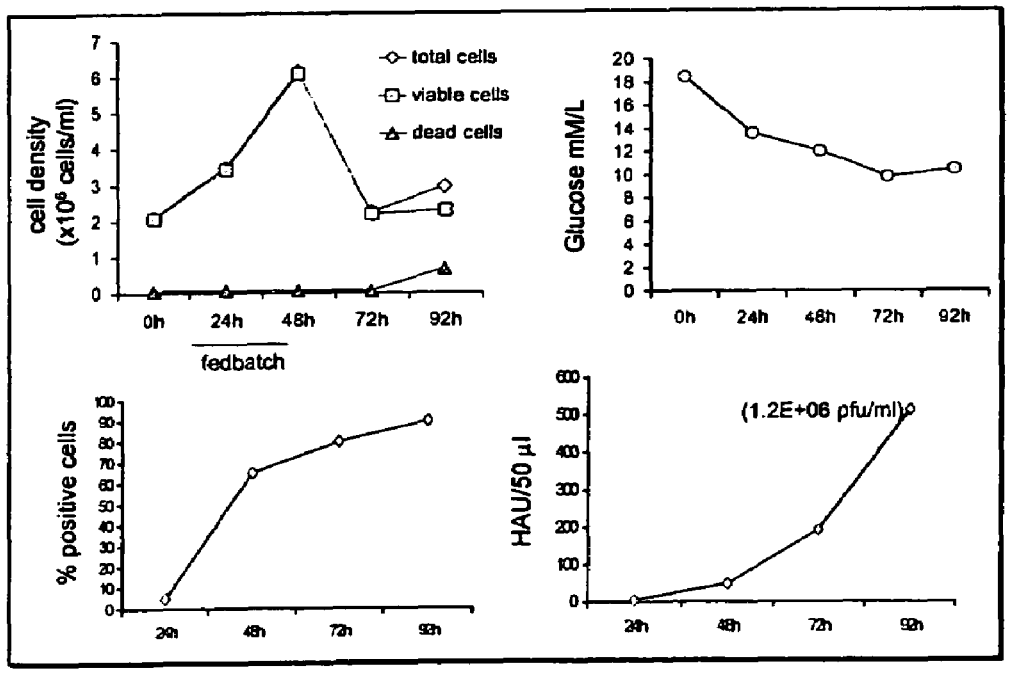
FIG. 23 consists of four graphs depicting infection of PER.C6 with A/Beijing/262/95 in a 2 liter cell suspension in a 3 liter bioreactor. PER.C6 cells viability (upper left), glucose concentration (upper right) and growth kinetics of the virus in the percentage of positively staining cells (lower left), and HAUs (lower right) are given.
Figure 24:
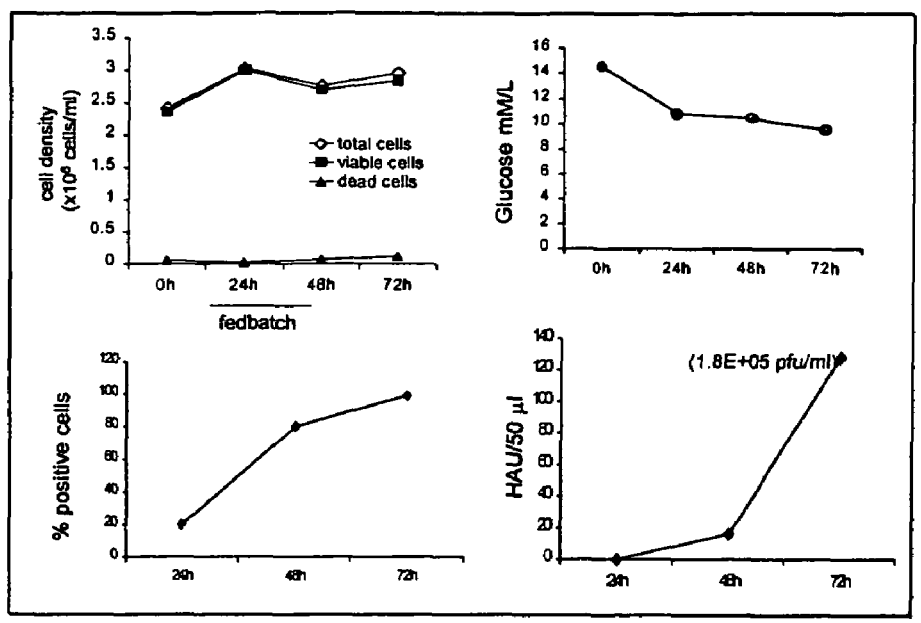
FIG. 24 consists of four graphs depicting infection of PER.C6 with B/Harbin/7/94 in a 2 liter cell suspension in a 3 liter bioreactor. PER.C6 cells viability (upper left), glucose concentration (upper right) and growth kinetics of the virus in the percentage of positively staining cells (lower left), and HAUs (lower right) are given.

Production of all three influenza viral batches were performed in three separate 3-liter hollow fiber fed-batch bioreactor systems with cell suspension volumes of 2 liters. Fed-batch was performed with the addition of the following solution: A total volume of 96 ml containing 50 m/v % glucose (NPBI), 50× essential amino acids without Gln (Gibco-BRL-Life Technologies), 200 mM glutamine (Gibco-BRL-Life Technologies) and 7.5 m/v % $NaHCO_3$ (Merck) was added once. Influenza infections were carried out at cell densities ranging from $1.8 \times 10^6$ to $2.6 \times 10^6$ viable cells/ml, in ExCell 525 serum-free medium containing 5 mg/ml trypsin-EDTA. PER.C6 cells were inoculated with the PER.C6-grown A/Sydney/5/97, A/Beijing/262/95 and B/Harbin/7/94 virus batches at different mois: $10^{-4}$ (A/Sydney/5/97) or $10^{-3}$ (A/Beijing/262/95 and B/Harbin/7/94) pfu/cell. During the virus production period, samples of 10 ml were taken every day to perform standard cell and viability counts, glucose concentration measurements, direct immunofluorescence and Hemagglutination assays. FIG. 22 (results from the A/Sydney/5/97-infected PER.C6 cells) shows the total and viability cell counts after infection with the virus (upper left panel), the glucose consumption (upper right panel), the percentage of positive cells in the direct immunofluorescence detection (lower left panel) and the HAUs (lower right panel). FIG. 23 (results from the A/Beijing/262/95-infected PER.C6 cells) shows the total and viability cell counts after infection with the virus (upper left panel), the glucose consumption (upper right panel), the percentage of positive cells in the direct immunofluorescence detection (lower left panel) and the HAUs (lower right panel). FIG. 24 (results from the B/Harbin/7/94-infected PER.C6 cells) shows the total and viability cell counts after infection with the virus (upper left panel), the glucose consumption (upper right panel), the percentage of positive cells in the direct immunofluorescence detection (lower left panel) and the HAUs (lower right panel). Virus-containing concentrates were stored at −80° C. until DSP.

In all three cases, the glucose consumption, viability and total cell counts of the PER.C6 cells were comparable. Also, the production levels of the three viruses, as measured by direct immunofluorescence, were similar. Although the HAU and infectivity titers differed between different strains, PER.C6 sustained replication of all influenza viruses that were tested here.

On the day of harvest of the entire batch (either at day 3 or at day 4 post-infection), viral supernatants were clarified by centrifugation at 2000 rpm in a table top centrifuge and concentrated ten-fold by ultra-filtration using a hollow fiber membrane cartridge of 750 kD cut-off (A/G Technology, JM Separations) following the protocols provided by the manufacturer. Influenza viruses were purified from the concentrated supernatants via two subsequent density centrifugation steps: a 25-70% block sucrose gradient (1.5 hours at 27K) followed by a continuous 25-70% sucrose gradient (four hours at 23K). Viral bands were diluted in approximately 50 ml of a Phosphate buffer and finally pelleted at 24,000 rpm in an ultracentrifuge. Viral pellets were dissolved in 1.5 to 2.3 ml of a Phosphate buffer, aliquoted and frozen at −80° C.

The formulation of inactivated Influenza vaccines is based on the amount (in micrograms) of the "immunologically active" HA protein, as measured by the SRID assay (Wood et al. 1977). The test was performed to characterize the HA content of the batches. At the same time, total amount of proteins was measured using the Lowry-based DC-protein assay kit (Biorad) following the procedures suggested by the manufacturer. It was found that HA constitutes about 20 to 30% of the total protein content of the virus preparation.

Example 11

In vivo Immunogenicity of Inactivated Vaccines Produced in Eggs and on PER.C6

Ferrets and mice represent two well-established animal models for studying influenza infection and have been used to determine the efficacy and immunogenicity of influenza vaccines. Using the mouse model test system, the immunogenicity produced by the PER.C6 and egg-derived trivalent vaccines containing A/Sydney/5/97, A/Beijing/262/95 and B/Harbin/7/94 are compared by analyzing sera of vaccinated animals by Hemagglutination inhibition assay. Using the ferret infection model, immunization is followed by a challenge with A/Sydney/5/97. Virus recovery on MDCK cells and Hemagglutination inhibition assay performed on the sera are used to compare the immunogenicity and efficacy of the two vaccines.

In Vivo Study in Mice

Ninety female Balb/C mice are divided into nine groups of ten mice. On day 0, up to 100 ml of blood is collected. The serum is separated and stored at −20° C. Each mouse is then vaccinated with the appropriate vaccine according to the schedule in Table I. On day 28, a further 100 ml of blood is taken. Serum is stored at −20° C. Each mouse is again vaccinated according to the schedule in Table I. On day 42, a 100 ml blood sample is taken and all mice are sacrificed. Serum is separated and frozen at −20° C. Hemagglutination Inhibition (HI) assays are conducted on serum samples from day 0, 28 and 42. All these assays are conducted in parallel for each day for both egg- and cell-grown viruses.

TABLE I

Immunogenicity test in mice.

| GROUP NUMBER | ANTIGEN TYPE | IMMUNIZATION VOLUME (ml) | VACCINATION ROUTE | TOTAL mg HA per dose |
|---|---|---|---|---|
| 1 | Egg trivalent whole virion | 0.5 | s.c. | 9.0 |
| 2 | Egg trivalent whole virion | 0.5 | s.c. | 3.0 |
| 3 | Egg trivalent whole virion | 0.5 | s.c. | 1.5 |
| 4 | Egg trivalent whole virion | 0.5 | s.c. | 0.15 |
| 5 | PER.C6 trivalent whole virion | 0.5 | s.c. | 9.0 |
| 6 | PER.C6 trivalent whole virion | 0.5 | s.c. | 3.0 |
| 7 | PER.C6 trivalent whole virion | 0.5 | s.c. | 1.5 |
| 8 | PER.C6 trivalent whole virion | 0.5 | s.c. | 0.15 |
| 9 | PBS | 0.5 | s.c. | 0 |

In Vivo Study in Ferrets

Eighteen adult female ferrets (albino or polecat) were divided in three groups of six divided as follows: Group 1 received the egg-derived test vaccine intramuscularly (IM), the animals were challenged with A/Sydney/5/97. Group 2 received the PER.C6-derived test vaccine IM, the animals were challenged with A/Sydney/5/97. Group 3 received the test vaccine diluent only and were challenged with A/Sydney/5/97. On days 0 and 28, the test vaccines were administered. On day 56, all the ferrets were infected intranasally with 0.5 ml of the A/Sydney/5/97 challenge virus at $TCID_{50}$ $10^3$. Nasal washes were performed and inflammatory cell counts, temperature and weights of the ferrets were monitored once daily from day 57 to 63. All animals were sacrificed on day 63. Serum was separated and stored at −20° C. The nasal wash samples were stored on ice and a nasal wash recovery cell count was performed using Trypan blue exclusion assay.

The titer of the virus obtained from the nasal wash samples was determined by measuring the virus recovery on MDCK cells. The Spearman and Karber (1931) calculation was used to calculate $TCID_{50}$ values. Hemagglutination inhibition analyses were conducted on serum samples taken on day 0, 28, 56 and 63. From this experiment, it was concluded that the PER.C6-derived test vaccine was effective.

Example 12

Characterization of HA Protein Derived from Influenza Virus Produced on PER.C6

In order to study the glycosylation of HA in PER.C6 cells, a batch of uncleaved HA (HA0) was generated. PER.C6 cells were infected with virus A/Sydney/5/97 (passage number 5 on PER.C6) at mois of 1, 0.1 and 0.01 pfu/cell in ExCell 525 medium containing trypsin-EDTA at the final concentration of 5 mg/ml. After one hour of incubation at 35° C., cells were washed twice with PBS to remove trypsin and incubated O/N at 35° C. and 10% $CO_2$, in the absence of trypsin. The next day, cell suspensions were harvested and centrifuged (500 g) and cell pellets were washed twice with medium. Viral supernatants were frozen at −80° C. and samples thereof were used in western blot assays as described to investigate the presence or absence of uncleaved HA protein. Uncleaved HA protein (HA0) consists of the two subunits: HA1 and HA2, that are connected via a disulfide bond. Since this disulfide bond can be disrupted by reduction with DTT, HA1 and HA2 can be separated and visualized on a reducing gel followed by western blots using antisera that recognize the subunits. If the HA protein consists only of HA0, one band will be visible that migrates slower through an SDS/PAGE gel as compared to the HA1 subunit and the fastest migrating HA2 subunit. The results shown in FIG. 25 suggest the presence of mainly uncleaved HA0 from PER.C6 infections when compared to the egg-derived positive control that was obtained from the NIBSC (UK). To confirm that the band detected was indeed uncleaved hemagglutinin, an HA0 sample was digested with different concentrations of trypsin ranging from 2.5 to 10 µg/ml in medium O/N at 37° C. The digested proteins were then loaded under reducing conditions on an SDS/PAGE gel followed by western blot analysis using the same antisera as described for FIG. 14. As shown in FIG. 26A, cleavage of the HA0 could be achieved, confirming the generation of uncleaved HA protein on PER.C6. Based on these results, an assay to determine trypsin activity in culture medium, using Influenza HA0 as substrate is developed.

Trypsin Activity Assay

To determine whether trypsin, present in the culture medium of an Influenza production run is still active, a trypsin activity assay has been developed. This assay is based on the measurement of the enzymatic activity of trypsin to cleave the substrate that is most relevant for influenza vaccine production: the HA0.

It was determined whether, in a culture of PER.C6 inoculated with Influenza B/Harbin/7/94 (moi $10^{-3}/10^{-4}$ pfu/cell), the trypsin remained active over the entire production run. To this end, 10 µl of supernatant taken at day 1, 2 and 3 post-infection were used to cleave 68 ng of the substrate that consisted of HA0 of Influenza A Sydney/5/97 virus, O/N at 37° C. Following digestion, protease inhibitors were added to a final concentration of 1× (complete protease inhibitor cocktail, Boehringer Mannheim) in 3× Laemli buffer with 150 mM DTT (Fluka). The samples were loaded on a 10% Tris-HCL SDS/PAGE gel (Biorad) and run. The western blot was performed as described. The results are shown in FIG. 26B, and demonstrate that in cultures of PER.C6 inoculated with Influenza B/Harbin virus, trypsin remained active during the entire production run as culture supernatants were able to cleave HA0 completely.

Example 13

Digestion of HA0 with N-Glycosidase F

The influenza virus HA protein is a glycoprotein that contains three to nine N-linked glycosylation oligosaccharide sites. The number of sites depends on the virus strain. The location of these sites is determined by the nucleotide sequence of the HA gene and since the viral genome of Influenza is replicated by an error-prone RNA polymerase, mutations that generate the addition or removal of glycosylation sites occur at high frequency. The composition and structure of the oligosaccharide chains present on the HA is then determined by the array of biosynthetic and trimming glycosylation enzymes provided by the host cell. Since glycosylation of HA plays an important role in virulence and vaccine efficacy, the properties of HA produced on Influenza infected PER.C6 was investigated. A digestion of A/Sydney/5/97 uncleaved HA0 protein with the N-glycosydase F enzyme was performed using protocols provided by the manufacturer to remove the seven oligosaccharides expected to be present on the A/Sydney/5/97 HA polypeptide. Influenza A/Sydney/5/97 was lysed with 1% Triton X-100 (Merck). Protease inhibitor was added to an aliquot of this lysed virus corresponding to 68 ng of HA, to a final concentration of 1× (Complete Protease Inhibitor Cocktail Boehringer Mannheim). This sample was incubated in the presence of 100 mM NaPO$_4$ pH 7, 10 mM EDTA (J. T. Baker), 1% SDS (J. T. Baker) and 1% B-mercaptoethanol (Merck). This was incubated for ten minutes at room temperature. The sample was diluted five times in mM NaPO$_4$ pH 7, 10 mM EDTA (J. T. Baker), 0.625% NP-40 and 1% B-mercaptoethanol (Merck). Of this, 40 µl was used for the glyco-F digestion. For this, 2 µl 1 U/µl of glyco-F (N-Glycosidase F, Boehringer) was added and incubated for a minimum period of 16 hours at 37° C. Then 3× Laemli buffer with 150 mM DTT (Fluka) was added to a final concentration of 1×. The samples were run on a 7.5% SDS/PAGE gel. The SDS-Page and western blot were performed as follows. In brief, the blot was blocked for 30 minutes at room temperature with block solution (5% nonfat dry milk powder, Biorad in TBST supplemented with 1% rabbit serum (Rockland) followed by three washes with TBST. Then, the blot was incubated with the anti- A/Sydney/5/97 HA antiserum (98/768 NIBSC) diluted 1/500 in 1% BSA/TBST with 5% rabbit serum (Rockland) overnight at room temperature. Again, the blot was washed eight times with TBST. Finally, the blot was incubated with the rabbit anti-sheep antiserum-HRP-labeled (Rockland) 1/6000 diluted in block solution for one hour at room temperature. After eight washes with TBST, the protein-conjugate complex was visualized with ECL (Amersham Pharmacia Biotech) and films (Hyperfilm, Amersham Life Science) were exposed. As shown in FIG. 27, treatment with the glycosidase-F enzyme clearly reduced the size of the protein with approximately 28-30 kD, being approximately the predicted loss of about 4 kD per oligosaccharide. The protein band depicted with an asterisk (*) is the de-glycosylated HA0 that migrates similarly to the HA1 subunit product obtained after cleavage of HA0 into HA1 and HA2 subunits (right lanes).

Example 14

Cleavage of HA0 with Accutase

Figure 28:
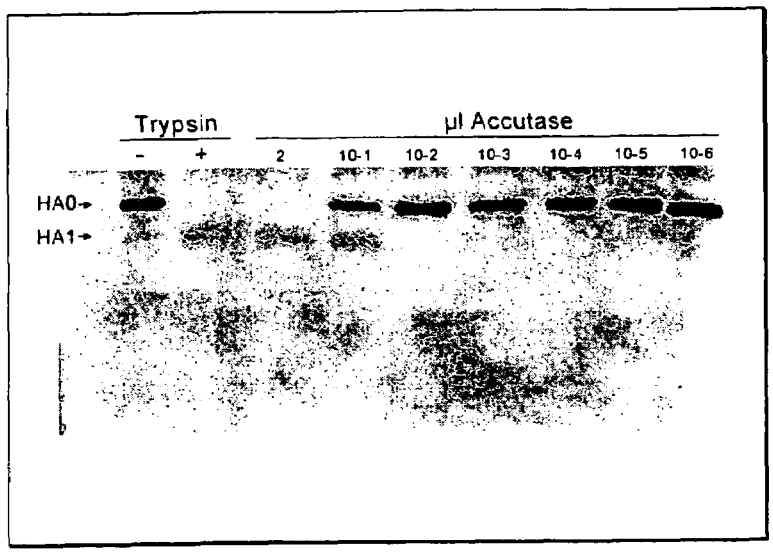
FIG. 28 is a Western blot analysis of A/Sydney/5/97 HA after Accutase digestion. Proteins are detected after incubation with the specific polyclonal anti-A/Sydney-HA antisera. On the left, HA0 before and after trypsin treatment, on the right, HA0 digested with decreasing amount of Accutase.

The possibility of replacing the mammalian-derived trypsin-EDTA with non-mammalian or recombinant proteins was investigated. Recently, a mixture of proteolytic and collagenolytic enzymes (Accutase™, PAA) from invertebrate species became available for routine cell culture. Due to its non-mammalian source, Accutase is free of prions, parvovirus, and other components that potentially can contaminate trypsin-EDTA solutions. No information regarding the type of proteases present in Accutase could be obtained to date. The cleavage of HA0 was studied using western blot analysis. A constant amount of HA0 protein, obtained by PER.C6 infected with A/Sydney/5/97 at an moi 1 pfu per cell without trypsin, was digested with serial dilutions of Accutase, O/N at 37° C. As a positive control, the same amount of HA0 digested with 100 ng of trypsin-EDTA was used. The digested proteins were then loaded on a 10% SDS-PAGE gel, under reducing conditions, for western blot analysis. As shown in FIG. 28, digestion with 2 ml of Accutase treatment resulted in complete cleavage of HA0; partial cleavage was observed using 0.2 ml. These results suggest that treatment with Accutase during influenza replication and production can replace trypsin-EDTA during influenza infections on PER.C6.

Example 15

Electron Microscopy Analysis of Influenza Viruses on PER.C6 Cells

Figure 29:
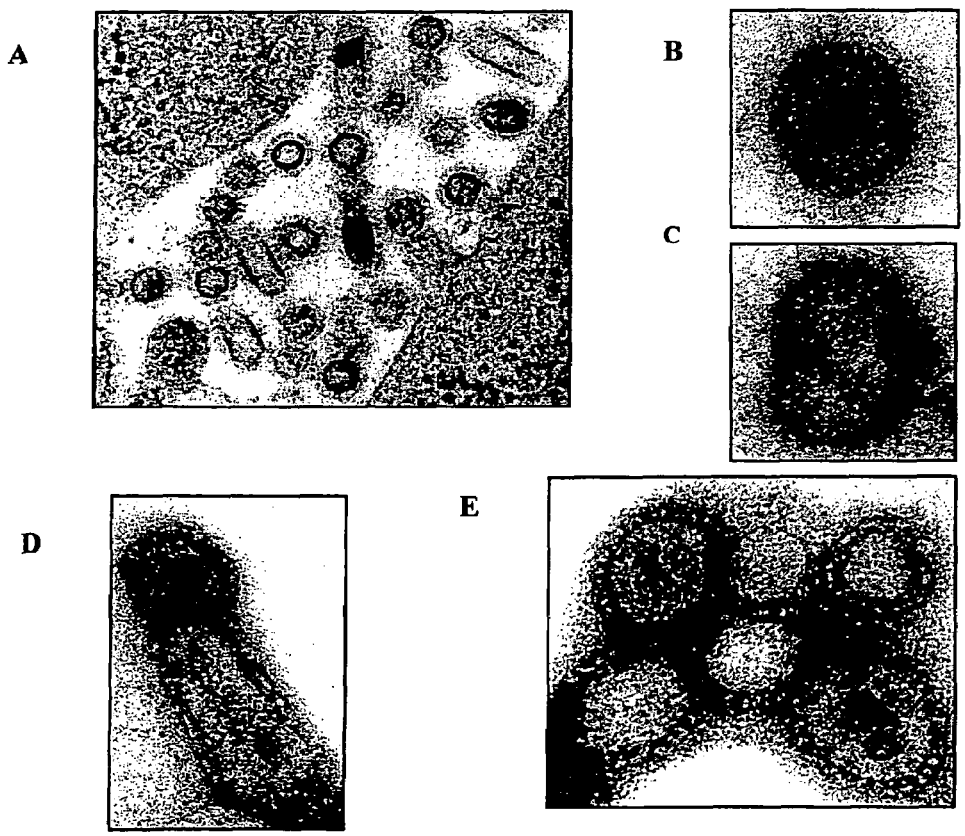
FIG. 29 consists of five portions (A through E) and depicts electron micrographs of Influenza A/Sydney/5/97. (A) PER.C6 cells 72 hours post-infection. (B and C) Negative staining on virus derived from infected PER.C6. (D and E) Negative staining of sucrose purified material.

Transmission electron microscopy studies were done on PER.C6 cells that were infected with the influenza strain A/Sydney/5/97, as well as on viral-containing supernatants and sucrose purified material, to determine the phenotype of this influenza virus produced on PER.C6. All methods that were used are well known to persons skilled in the art. FIG. 29 shows that the last stages of the virus life cycle are represented by budding and release of enveloped virions from the cytoplasmic membrane. Spikes corresponding to the HA and NA viral proteins were detected, ornamenting the periphery of the virion particles. The figure also shows the characteristic pleiomorphism of influenza viruses.

Example 16

Infection of PER.C6 with a Large Variety of Influenza A and B Virus Strains

The use of PER.C6 as a platform technology for the production of influenza vaccine would preferably require PER.C6 to support the growth of a wide range of strains of different influenza subtypes.

Figures 30A, 30B:
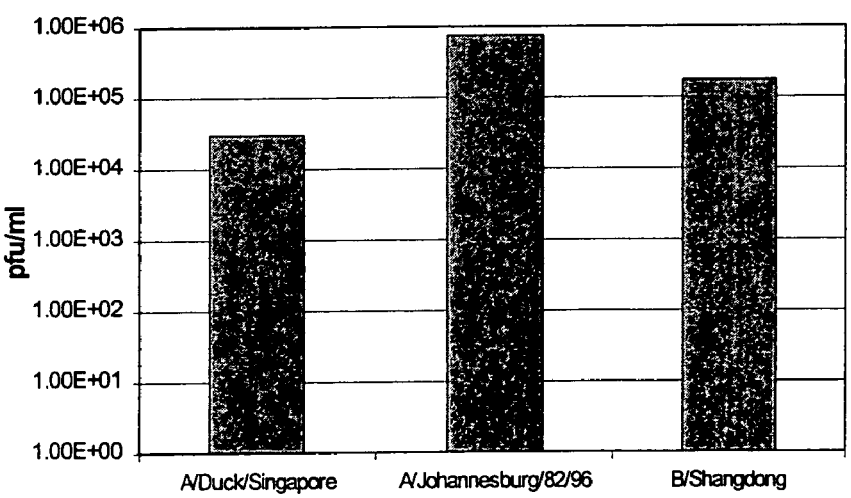
FIG. 30A identifies different Influenza A and B strains tested on PER.C6 cells.
FIG. 30B is a bar graph depicting infectivity titers of three depicted A- and B-type influenza viruses derived from infected PER.C6 cells.

Static suspension cultures of PER.C6 cells that were grown in T25 flasks and/or in six-well plates in ExCell 525 medium, were infected at a cell density of $10^6$ cells/ml with 16 different strains of influenza viruses (FIG. 30A). These strains comprised several H3N2, H1N1, B type and Avian strains. Infections were performed in the presence of 5 μg/ml of trypsin. The viruses were obtained from NIBSC as egg-passaged wt or reassortant strains and are noted. Infection was performed with a virus dilution recommended by the NIBSC in the product sheets that were delivered with the different strains. All viruses tested were capable of propagation on PER.C6 as visualized by immunofluorescence (data not shown) and titration of supernatant fluids in pfu assay (FIG. 30B).

These results show that even influenza strains (depicted by an asterisk), such as A/Johannesburg/33/94, B/Beijing/184/93 and A/Duck/Singapore-Q/F119-3/97, which are normally very difficult to produce on embryonated eggs, can replicate and be produced on PER.C6 cells.

Example 17

Generation of Herpes Simplex Type 1 (HSV-1) Virus, Herpes Simplex type 2 (HSV-2) Virus and Measles Virus on PER.C6

It was tested whether viruses other than influenza virus and adenovirus, for example, Herpes Simplex Virus type 1 and 2 and measles virus, could also replicate on PER.C6. Vaccines that are derived from these PER.C6-grown viruses and that induce neutralizing effects in humans for protection against wt infections, are generated from the PER.C6-grown virus batches. The strains that were obtained from ATCC and used for infection of PER.C6 cells are depicted in Table II.

TABLE II

Herpes simplex virus and Measles strains that were obtained from the ATCC and that were used for infection of PER.C6 cells.

| Virus | Strain | ATCC cat no. | Lot no. | Passage history | Titer |
|---|---|---|---|---|---|
| Herpes Simplex Type 1 | Macintyre | VR-539 | 1327850 | y.s./12, PR RabK/5, Mb/1, PrRabK/5, Vero/4, Vero (ATCC CCl-81)/1 | $10^{6.75}$ TCID50/200 μl |
| Herpes Simplex Type 2 | MS | VR-540 | 216463 | Sheep choroid plexus/?, HeLa/?, PrRabK/7, Vero (ATCC CCl-81)/3 | $10^{7.5}$ TCID50/200 μl |
| Measles | Edmonston | VR-24 | 215236 | HK/24, HuAm/40, MRC-5/1, MRC-5 (ATCC CCL-171)/1 | $10^4$ TCID50/ml |

To test whether HSV-1, HSV-2 and measles viruses obtained from the ATCC could replicate and be produced on PER.C6, passage number 46 cells were seeded in Labtek chambers, coated with Poly-L-Lysine using known methods, at $10^5$ cells/well. Monkey-derived Vero cells (obtained from ATCC) were cultured at passage number 137 and were used as positive controls and seeded at a density of $2.5 \times 10^4$ cells/well. At day 0, when wells with PER.C6 cells were 60% and Vero cells 80% confluent, cells were infected with different mois ($10^{-3}$, $10^{-2}$, $10^{-1}$ and 1 $TCID_{50}$ per cell). At daily intervals upon infection, cells were fixed and assayed in immunofluorescence using FITC-conjugated type-specific monoclonal antibodies using a kit (Imagen Herpes Simplex Virus (HSV) Type 1 and 2, Dako- and FITC-conjugated antibodies against the HA and matrix protein of measles virus (measles IFA kit, Light diagnostics), following the procedures suggested by the manufacturer. The antisera are directed against HSV-1 and −2 and Measles virus antigens.

Figure 31:
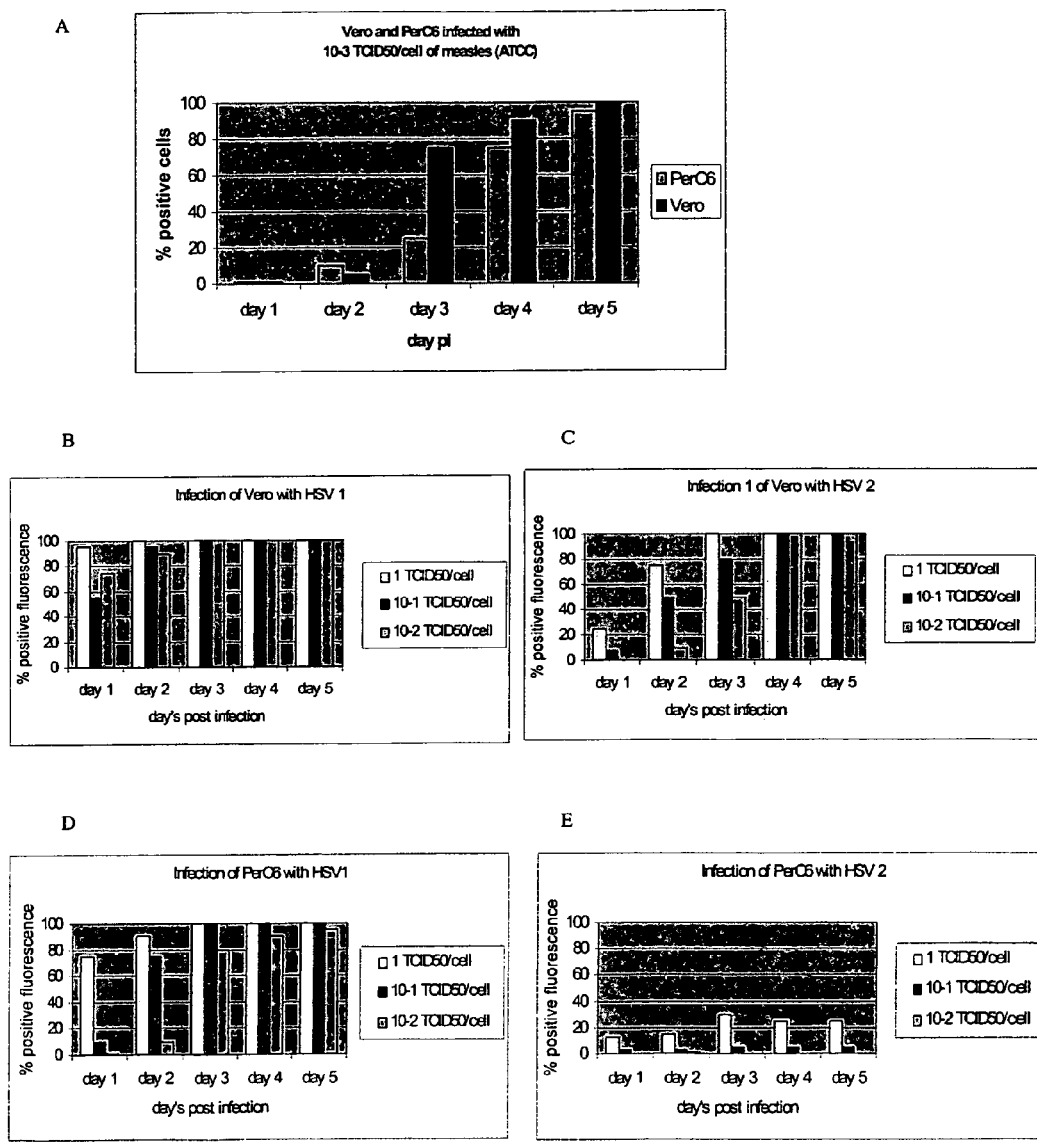
FIG. 31 consists of five bar graphs (A through E) depicting immunofluorescence of PER.C6 and Vero cells infected with viruses other than influenza. (A) Positively staining cells upon infection with Measles virus. (B) Positively staining cells upon infection of Vero cells with HSV-1 virus. (C) Positively staining cells upon infection of Vero cells with HSV-2 virus. (D) Positively staining cells upon infection of PER.C6 cells with HSV-1 virus. (E) Positively staining cells upon infection of PER.C6 cells with HSV-2 virus.

The results summarized in FIG. 31 show that PER.C6 is permissive for HSV-1 (FIG. 31, portion D), HSV-2 (FIG. 31, portion E) and measles virus (FIG. 31, portion A) infections. Furthermore, the kinetics suggest that these viruses replicate on PER.C6 in an moi-dependent manner.

Figure 32:
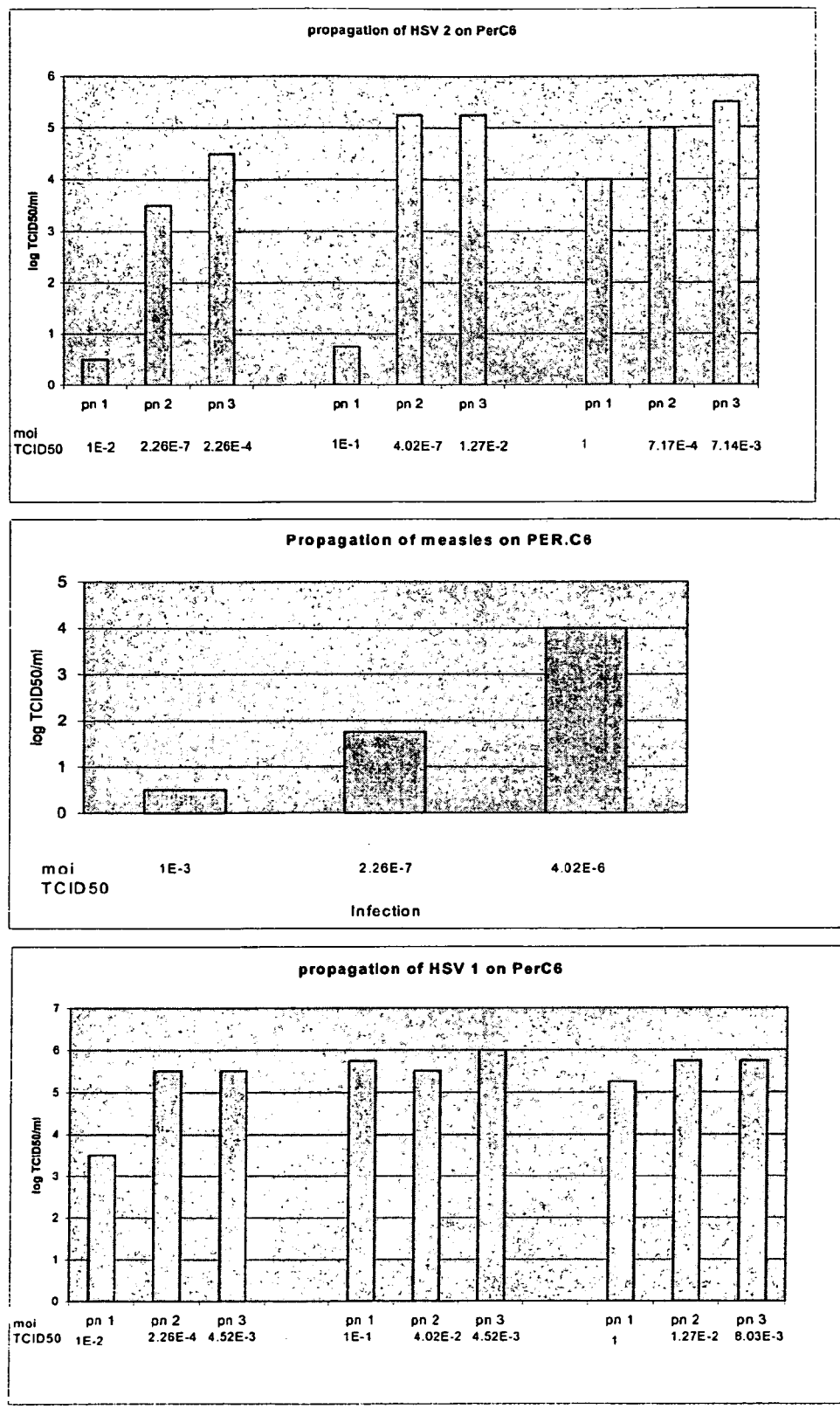
FIG. 32 consists of upper, middle and lower portions, depicting infectivity titers determined after propagation of measles virus (middle panel), HSV-1 (bottom panel) and HSV-2 (top panel) virus on PER.C6 cells.

Next, it was investigated whether HSV-1, -2 and measles virus could be propagated on PER.C6. To this end, cells were infected with moi of 0.01, 0.1 and 1 $TCID_{50}$/cell for HSV-1 (FIG. 32 lower portion) and HSV-2 (FIG. 32 upper portion) and an moi of 0.001 $TCID_{50}$/cell for measles virus (FIG. 32 middle portion) (passage number 1). At the occurrence of almost complete CPE, cells and supernatants were harvested, quickly frozen in liquid $N_2$, and thawed. After this, clarified supernatants were passaged blindly using approximately 100 μl to PER.C6 (this is passage number 2). After reaching almost complete CPE again, a third passage (passage number 3) was performed in a similar manner. The mois of the passage number 2 and 3 were determined in retrospect by $TCID_{50}$ assays.

The results of these experiments show that Herpes Simplex Virus type 1 and −2 and Measles viruses can be replicated on PER.C6 and that replication and propagation can even occur when mois as low as $10^{-7}$ are used.

Example 18

Screening of Rotavirus for Replication on PER.C6

Figure 33:
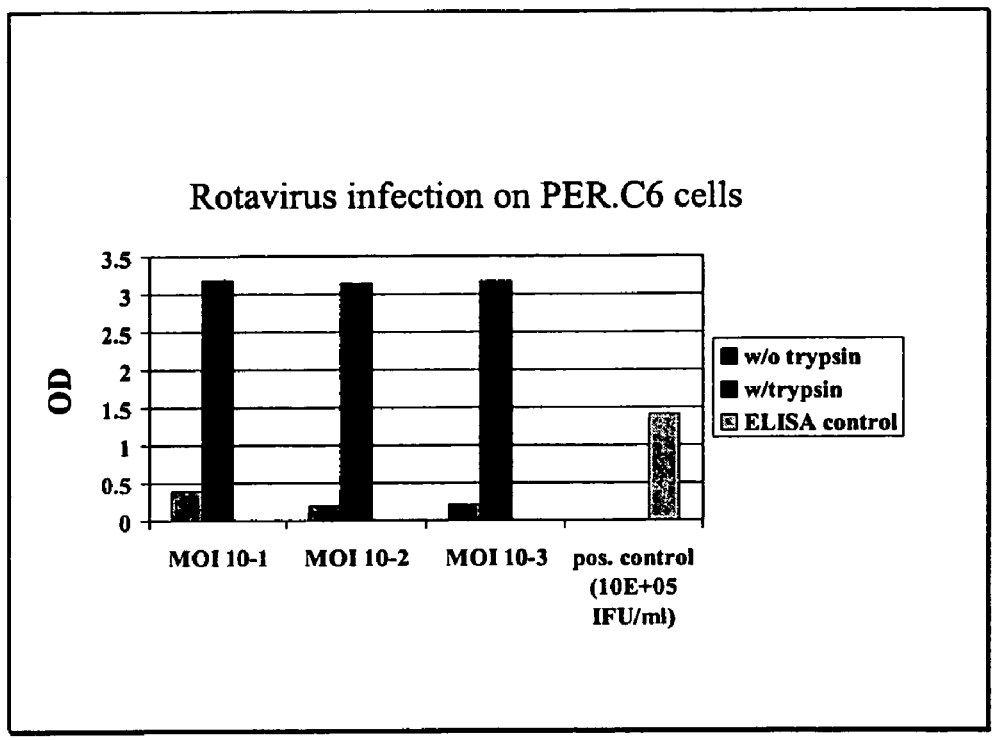
FIG. 33 consists of upper and lower panels and depicts replication of rotavirus after infection of PER.C6 (top panel) and Vero (bottom panel) cells with different mois as measured by ELISA in crude supernatants.
Figure 33:
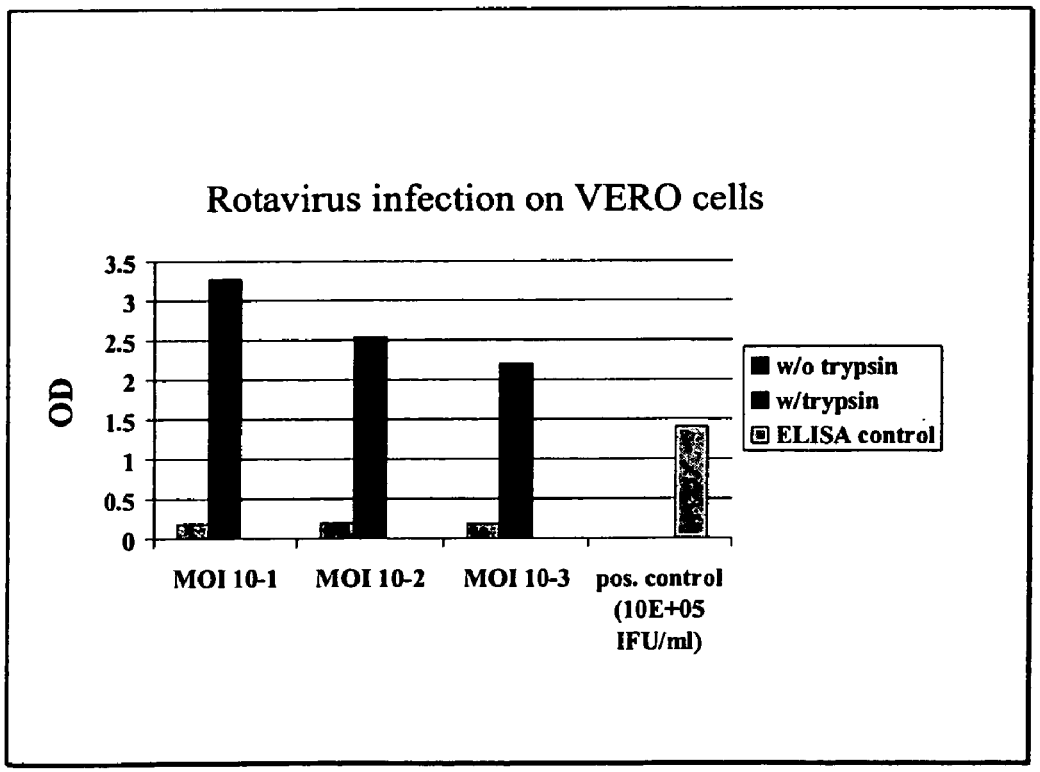

To test whether PER.C6 could also support the replication of a rotavirus, PER.C6 cells were infected with a rhesus rotavirus (MMU 18006; ATCC#VR-954; strain S:USA:79:2; lot # 2181153). PER.C6 cells (passage number 41) were cultured at a density of $1\times10^5$ per ml and monkey-derived Vero cells (obtained from ATCC, passage number 139) were cultured at a density of $2.5\times10^4$ per ml and subsequently seeded in Labtek chambers that had been pre-coated with poly-L-Lysine as previously identified. Cells were infected with an moi of 1 $TCID_{50}$/cell of Rhesus rotavirus in the presence and absence of 2 µg/ml of trypsin-EDTA. After 90 minutes of infection, cells were washed with ExCell 525 medium and further incubated at 37° C. at 10% $CO_2$ in a humidified atmosphere. On five consecutive days following infection, samples of supernatants were harvested, clarified from cells and cell debris by centrifugation at 2000 rpm in a table top centrifuge and analyzed in an ELISA specific for rotavirus (IDEIA Rotavirus, Dako). The results depicted in FIG. 33 clearly show that Rhesus rotavirus replicates on PER.C6.

Example 19

Growth of Pandemic Influenza Strains on E1 Transformed Cells

In FIG. 30A, it was outlined which influenza strains could be grown on mammalian E1-transformed cells, such as PER.C6® cells. Clearly, the H3N2 and H1N1 strains as well as the influenza B strains and the avian strains could all be grown to significant titers on PER.C6 cells.

It is known that only a limited number of influenza strains generally cause disease in humans. However, it is now well established that also strains that generally only occur in birds can, through re-assortment in man, become infectious for humans and be transferred from one human being to another. Such bird-derived influenza strains can cause so-called "pandemics" and infect millions of people around the world and cause countless numbers of casualties. One major example of such pandemic was the Spanish flu that killed millions around 1918. In Table III (partly taken from: "Avian influenza: assessing the pandemic threat" publication from the World Health Organization (January 2005)), previous worldwide outbreaks of highly pathogenic avian influenza strains are given. In Table IV (from the same source), documented human infections with avian influenza viruses are listed. From these tables, it is at least clear that at least the following virus strains are a threat to the well being of birds and humans worldwide: H5N1, H5N2, H5N8, H5N9, H7N1, H7N3, H7N4, H7N7, and H9N2. On top of this, it has recently been established through reverse genetics that the Spanish flu in 1918-1919 was caused by the H1N1 variant (Tumpey T M et al. (2005) *Science* 310:77-80).

To date, no vaccines exist against the pandemic strains listed in Table III and IV. It is therefore highly preferred to generate vaccines against influenza strains that are not only involved in the yearly influenza outbreaks for which numerous vaccines from different vaccine producers are available, albeit only produced on embryonated hens' eggs, but also against the strains that are associated with pandemic outbreaks or that have the potential to be associated with a pandemic outbreak (as listed above). Generally, these strains have a H5, H7 or a H9 haemagglutinin. Clearly, it cannot be excluded that new combinations of haemagglutinin and neuraminidase will arise and mutate to become highly pathogenic in addition to the combinations listed above.

Here, it was tested whether a number of these strains could be grown on E1-transformed mammalian cells, such as the human retinoblast-derived PER.C6 cells. The strains that were used as examples were H5N1, H7N7 and H9N2.

Figure 34:
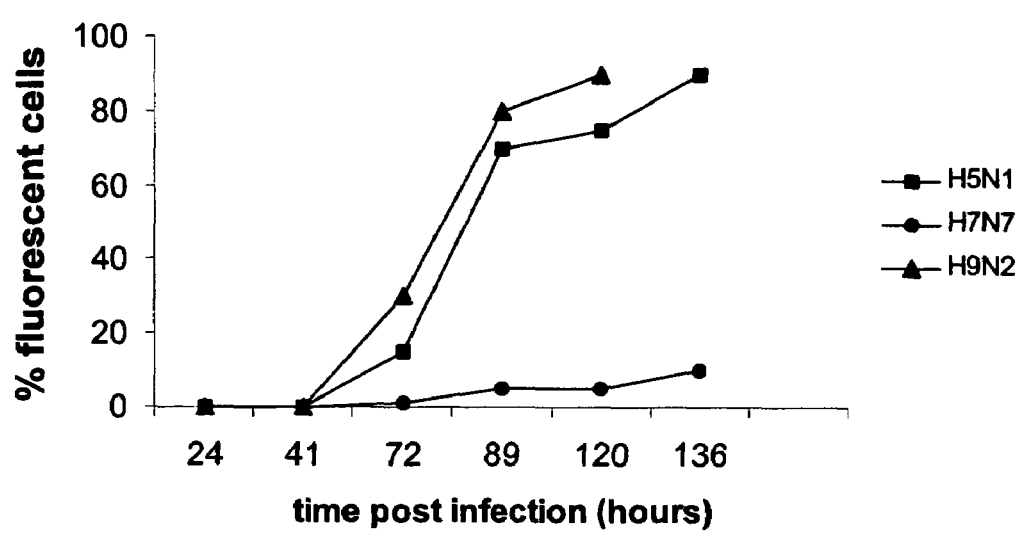
FIG. 34 is a graph depicting data from Example 19, showing that H5N1 and H9N2 infected almost all cells, while H7N7 was only detected in 10% of the cells.

For this, H5N1 (A/Hong Kong/97) was initially grown on MDCK cells and subsequently inoculated in PER.C6 cell cultures. H7N7 (A/Chicken/Netherlands/03) and H9N2 (A/Chicken/Saudi Arabia/00) strains were initially grown on embryonated eggs and subsequently inoculated in PER.C6 cell cultures, generally as described herein. Fluorescence was determined as outlined above. FIG. 34 indicates that H5N1 and H9N2 infected almost all cells as nearly 100% of the cells expressed the virus proteins. H7N7 was only determined in approximately 10% of the cells. Since the titers of the viruses were not known, it might be that the titer of the H7N7 batch was too low to obtain a proper result.

Figure 35:
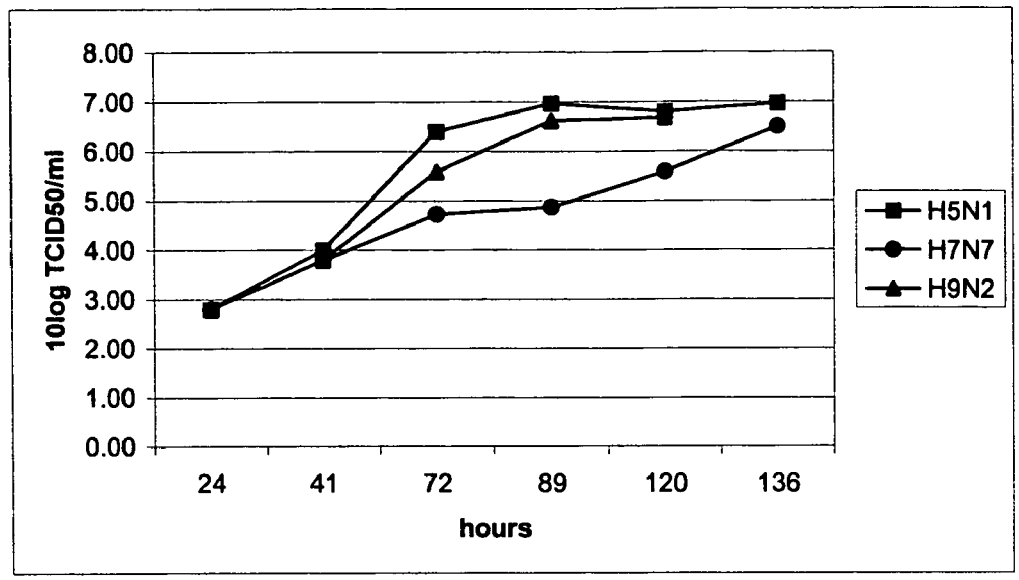
FIG. 35 includes two graphs also depicting data from Example 19, showing that the E1-transformed cells are able to sustain growth of all three tested influenza strains that are associated with a pandemic outbreak.
Figure 35:
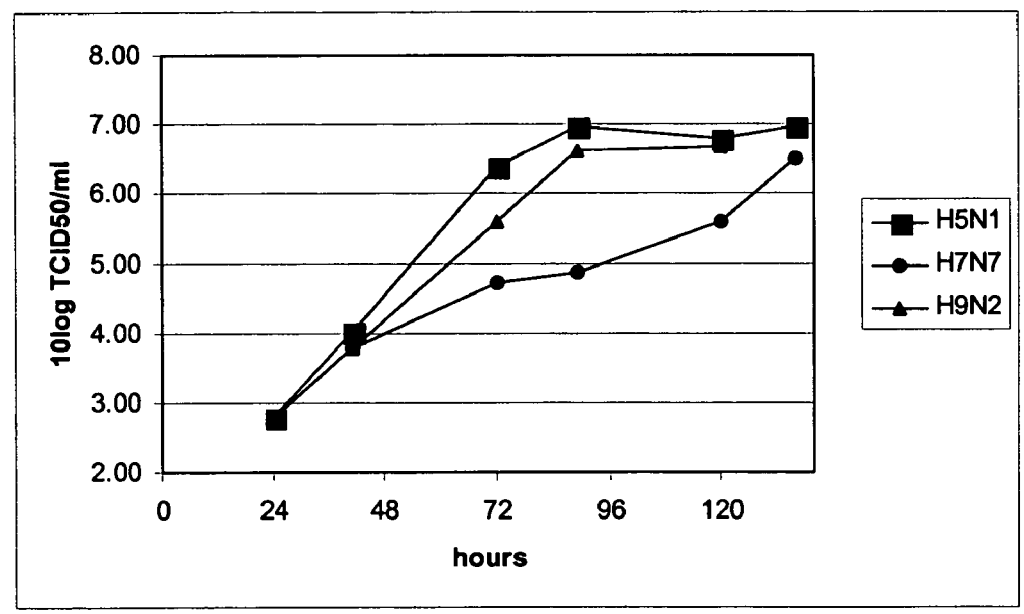

Subsequent experiments on PER.C6 cells were generally performed as described above, in which the inoculation titers were m.o.i. 0.0001 (H5N1 and H7N7) and 0.0006 (H9N2). Infection rates were determined by TCID50. This experiment was performed twice. The TCID50 was determined using methods known to the person skilled in the art, on MDCK cells, as described above. The results are given in FIG. 35. Clearly, the E1-transformed PER.C6 cells are able to sustain the growth of all three strains that are associated with a pandemic outbreak, indicating that PER.C6 cells are a suitable substrate to produce influenza viruses based on these strains and to make vaccines against pandemic influenza strains.

Figure 36:
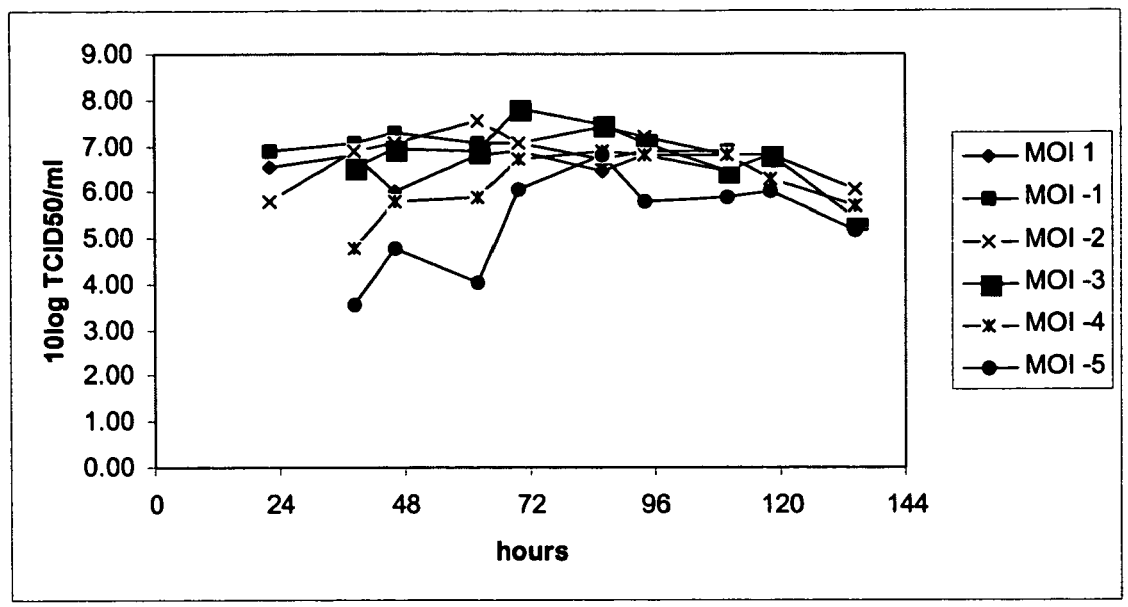
FIG. 36 includes a graph depicting further data from Example 19, showing that at even at very low inoculation titers, good results can be achieved.

In a next experiment, different m.o.i.'s were applied using the H5N1 strain. PER.C6 cells were inoculated with m.o.i. 1, 0.1, 0.01, 0.001, 0.0001 and 0.00001 (given as 1, −1, −2, −3, −4 and −5). TCID50 values were again determined with MDCK cells. The results are shown in FIG. 36 and clearly indicate that even at very low inoculation titers good results can be achieved, as an m.o.i. of 0.01 gave the best results after three days upon inoculation. These results clearly show that PER.C6 cells are very suitable for the growth of pandemic influenza strains in tissue culture thereby circumventing the need for vaccine production using embryonated hen's eggs.

The invention therefore also relates to vaccines comprising influenza viruses that are replicated and grown on E1-transformed cells, exemplified by PER.C6 cells. Influenza vaccines may be produced by attenuating produced viruses, inactivating produced viruses or disintegrating produced viruses, wherein it is preferred that the viruses are split and the two major immunogenic components of the virus, haemagglutinin and neuraminidase are further purified and finally mixed with a therapeutically acceptable excipient, such as a therapeutically acceptable buffer or salt solution. Such therapeutically acceptable excipients or carriers are well known in the art. Vaccines may comprise adjuvants, such as aluminum-based adjuvants (aluminum hydroxide and/or aluminum phosphate). Preferably, the split influenza virus containing vaccines, according to the invention, also comprise an adjuvant to stimulate the immune response. The viruses obtained by the methods applying adenovirus E1-transformed cells are typically harvested after 2 to 10 days after inoculation and after harvest attenuated, inactivated or split by methods known to the person skilled in the art. Harvest may be accompanied by sonication to release more virus. Also, contaminating nucleic acids are typically removed by a nuclease treatment, such as Benzonase. Formalin or BPL may be used for inactivation. Triton is preferably used for obtaining a split virus. The split-virus based vaccines typically comprise the antigenic determinants based on the HA and the NA components of the viral coat, which components are typically purified by one or more chromatography steps, including anion and/or cation exchange resins and several concentration, zonal centrifugation and dia- and/or ultra-filtration steps. The formulation of the vaccine is such that the components are therapeutically acceptable in mammals, and preferably in humans.

Although the invention has been described with a particular amount of detail and with respect to particular examples, the scope of the invention is to be determined by the appended claims.

TABLE III

Outbreaks of highly pathogenic avian influenza virus strains around the world.

| period | Location | strain |
|---|---|---|
| 1959 | Scotland, United Kingdom | H5N1 |
| 1963 | England, United Kingdom | H7N3 |
| 1966 | Ontario, Canada | H5N9 |
| 1976 | Victoria, Australia | H7N7 |
| 1979 | Germany | H7N7 |
| 1979 | England, United Kingdom | H7N7 |
| 1983-1985 | Pennsylvania, USA | H5N2 |
| 1983 | Ireland | H5N8 |
| 1985 | Victoria, Australia | H7N7 |
| 1991 | England, United Kingdom | H5N1 |
| 1992 | Victoria, Australia | H7N3 |
| 1994 | Queensland, Australia | H7N3 |
| 1994-1995 | Mexico | H5N2 |
| 1994 | Pakistan | H7N3 |
| 1997 | Hong Kong | H5N1 |
| 1997 | New South Wales, Australia | H7N4 |
| 1997 | Italy | H5N2 |
| 1999-2000 | Italy | H7N1 |
| 2002 | Hong Kong | H5N1 |
| 2002 | Chile | H7N3 |
| 2003 | Netherlands | H7N7 |
| 2004 | Pakistan | H7N3 |
| 2004 | Texas, USA | H5N2 |
| 2004 | British Colombia, Canada | H7N3 |
| 2004 | South Africa | H5N2 |
| 2003-2005 | South East Asia | H5N1 |
| 2005 | Turkey | H5N1 |
| 2005 | Romania | H5N1 |

TABLE IV

Documented human infections with avian influenza viruses.

| period | location | strain | cases | deaths |
|---|---|---|---|---|
| 1959 | USA | H7N7 | 1 | 0 |
| 1995 | United Kingdom | H7N7 | 1 | 0 |
| 1997 | Hong Kong | H5N1 | 18 | 6 |
| 1998 | China | H9N2 | 5 | 0 |
| 1999 | Hong Kong | H9N2 | 2 | 0 |
| 2003 | Hong Kong | H5N1 | 2 | 1 |
| 2003 | Netherlands | H7N7 | 89 | 1 |
| 2003 | Hong Kong | H9N2 | 1 | 0 |
| 2004 | Vietnam | H5N1 | 33 | 25 |
| 2004 | Thailand | H5N1 | 17 | 12 |
| 2004 | Canada | H7N3 | 2 | 0 |

REFERENCES

Bachmayer H. Selective solubilization of hemagglutinin and neuraminidase from Influenza virus. *Intervirology* 1975; 5:260-272.

Brands R., A. M. Palache, and G. J. M. van Scharrenburg. Madin Darby Canine Kidney (MDCK)-cells for the production of inactivated Influenza subunit vaccine. Safety characteristics and clinical results in the elderly. In: Brown L. E., E. W. Hampson, R. G. Webster, editors. Option for the control of Influenza III. *Amsterdam Elsevier,* 1996. P. 683-693.

Brands R., A. M. Palache, and G. J. M. van Scharrenburg. Development of Influenza subunit vaccine produced using mammalian cell culture technology. In M. J. T. Carrondo, B. Griffths, J. L. P. Moreira, editors. Animal cell technology: from vaccines to genetic medicine. Dordrecht: Kluwer Academic Publishers, 1997:165-167.

Gubareva L. V., J. M. Wood, W. J. Meyer, J. M. Katz, J. S. Robertson, D. Major, and R. G. Webster. Co-dominant mixtures of viruses in strains of Influenza virus due to host cell variation. *Virol.* 1994; 199:89-97.

Govorkova E. A., M. N. Matrosovich, A. B. Tuzikov, N. V. Bovin, C. Gerdil, B. Fanget, and R. G. Webster. Selection of receptor-binding variants of human Influenza A and B viruses in baby hamster kidney cells. *Virology* 1999 15; 262(1):31-8

Herrero-Euribe L. et al. Replication of Influenza A and B viruses in human diploid cells. *J. Gen. Virol.* 1983; 64:471-475.

Karber G. Beitrag zur kollektiven behandlung pharmakologischer reihenversuche. *Exp. Pathol. Pharmakol.* 1931; 162,480-483.

Kodihalli S., D. M. Justewicz, L. V. Gubareva, and R. G. Webster. Selection of a single amino acid substitution in the hemagglutinin molecule by chicken eggs can render Influenza A virus (H3) candidate vaccine ineffective. *J. Virol.* 1995; 69:4888-4897.

Kirstner O., K. Muller, and C. Scholtissek. Differential phosphorylatian of the nucleoprotein of Influenza A viruses. *J. Gen. Virol.* 1998; 70:2421-2431.

Marsha A. et al. *Pharmacotherapy* 19 (11):1279-1295, 1999: Rotavirus disease and its prevention in infants and children.

Murphy B. R. and R. G. Webster. *Orthomyxoviruses. In: Fields Virology*, chapter 46, 1397. Eds. B. N. Fields, D. M. Knipe, and P. M. Howley, et al., Lippincott-Raven Publishers, Philadelphia 1996.

Newman R. W., R. Jenning, D. L. Major, J. S. Robertson, R. Jenkins, C. W. Potter, I. Burnett, L. Jewes, M. Anders, D. Jackson, and J. S. Oxford. Immune response of human volunteers and animals to vaccination with egg grown Influenza A (H1N1) virus is influenced by three amino acid substitutions in the hemagglutinin molecule. *Vaccine* 1993; 11:400-406.

Palache A. M., R. Brands, and G. J. M. van Scharrenburg. Immunogenecity and reactogenecity of Influenza subunit vaccines produced in MDCK cells or fertilized chicken eggs. *J. Infect. Dis.* 1977; 176:S20-S23.

Robertson J. S., P. Cook, C. Nicolson, R. Newman, and J. M. Wood. Mixed populations in Influenza vaccine strains. *Vaccine* 1994; 12:1317-1320.

Robertson J. S., J. S. Bootman, C. Nicolson, D. Major, E. W. Robertson, and J. M. Wood. The hemagglutinin of Influenza B virus present in clinical material is a single species identical to that of mammalian cell-grown virus. *Virol.* 1990; 179:35-40

Robertson J. S., J. S. Bootman, R. Newman, J. S. Oxford, R. S. Daniels, R. G. Webster, and G. C. Schild. Structural changes in the hemagglutinin which accompany egg adaptation of an Influenza A(H1N1) virus. *Virol.* 1987; 160:31-37.

Schild G. C., J. S. Oxford, J. C. de Jong, and R. G. Webster. Evidence for host-cell selection of Influenza virus antigenic variants. *Nature* 1983; 303:706-709.

Schulman J. L., and P. Palese. Virulence factors of Influenza A viruses: WSN virus neuraminidase required for plaque production in MDBK cells. *J. Virol.* 1977; 24:170-176.

Sugiara A., and M. Ueda. Neurovirulence of Influenza virus in mice. I. Neurovirulence of recombinants between virulent and avirulent virus strains. *Virol.* 1980; 101:440-449, 495, 271.

Tobita K., A. Sugiara, C. Enomoto, and M. Furuyama. Plaque assay and primary isolation of Influenza A viruses in an established line of canine Kidney cells (MDCK) in the presence of trypsin. *Med. Microbiol. Immunol.* 1975; 162: 9-14.

Williams S. P., and J. S. Robertson. Analysis of restriction to the growth of non-egg-adapted human Influenza in eggs. *Virol.* 1993; 196:660665.

Wood J. M., G. C. Schild, R. W. Newmann, and V. Seagroatt. Application of an improved single-radial-immunodiffusion technique for the assay of hemagglutinin antigen content of whole virus and subunit Influenza vaccines. *Dev. Biol. Stand.* 1977 1-3; 39:193-20.

What is claimed is:

1. A method for producing an influenza virus and/or influenza viral proteins for use as a vaccine, said method comprising:
   providing a cell that is derived from a human embryonic retinoblast by immortalization with at least one gene product of an adenoviral E1 gene;

providing said cell with nucleic acid encoding an influenza virus;

culturing said cell in a suitable medium and allowing for propagation of said influenza virus; and harvesting said influenza virus and/or influenza viral proteins from said suitable medium and/or said cell.

2. The method according to claim 1, wherein a sequence encoding the at least one gene product of the adenoviral E1 gene is present in the genome of said cell.

3. The method according to claim 1, wherein said cell does not produce adenoviral structural proteins.

4. The method according to claim 1, wherein said cell is cultured in suspension.

5. The method according to claim 1, wherein said cell is cultured in the absence of serum.

6. The method according to claim 1, wherein said cell is a cell as deposited under ECACC no. 96022940.

7. The method according to claim 1, wherein said influenza virus is harvested, the method further comprising the step of attenuating, inactivating or disrupting said harvested virus.

8. The method according to claim 7, wherein said virus is disrupted, further comprising the step of purifying haemagglutinin and/or neuraminidase proteins from said influenza virus.

9. A method for producing an influenza vaccine, said method comprising the steps of:
producing hemagglutinin and/or neuraminidase proteins according to the method of claim 8; and
mixing said proteins with a therapeutically acceptable excipient.

10. A process for producing haemagglutinin proteins and/or neuraminidase proteins of an influenza virus, said process comprising:
providing a cell, wherein said cell is a human embryonic retinoblast cell that has been immortalized by at least one gene product of an adenoviral E1 gene;
providing said cell with nucleic acid encoding an influenza virus;
culturing said cell in a medium suitable for culturing the cell,
propagating said influenza virus in said cell;
disrupting the propagated influenza virus, and
isolating haemagglutinin proteins and/or neuraminidase proteins from the disrupted influenza virus.

11. The method according to claim 1, wherein the step of providing the cell with a nucleic acid encoding an influenza virus comprises infecting the cell with the influenza virus.

12. The process of claim 10, wherein the step of providing the cell with a nucleic acid encoding an influenza virus comprises infecting the cell with the influenza virus.

13. A process for producing an influenza vaccine, the process comprising:
producing hemagglutinin and/or neuraminidase proteins according to the process of claim 10; and
mixing said hemagglutinin and/or neuraminidase proteins with a therapeutically acceptable excipient.

14. The process of claim 1, wherein said influenza virus is an influenza virus strain that is associated with a pandemic outbreak, or has the potential to be associated with a pandemic outbreak.

* * * * *

UNITED STATES PATENT AND TRADEMARK OFFICE
CERTIFICATE OF CORRECTION

PATENT NO.         : 7,521,220 B2
APPLICATION NO.    : 11/256352
DATED              : April 21, 2009
INVENTOR(S)        : Maria G. Pau, Alphonsus G. C. M. UytdeHaag and Govert J. Schouten It is certified that error appears in the above-identified patent and that said Letters Patent is hereby corrected as shown below:

On the title page:
In ITEM (63) Related U.S. Application Data
    2nd line      change "abandoned." to --abandoned, which is a continuation-in-part of application No. 09/449,854, filed on Nov. 26, 1999.--

In ITEM (56) References Cited
    OTHER PUBLICATIONS
    Page 2, 1st Column, line 13,
      3rd line of the 3rd entry,      change "PIX Mutant" to --pIX Mutant--

Page 2, 1st Column, line 24,
      3rd line of the 7th entry,      change "pp. 397-387," to --pp. 379-387,--

Page 2, 1st Column, line 52,
      2nd line of the 17th entry,      change "applicaiton" to --application--

Page 2, 1st Column, line 61,
      3rd line of the 20th entry,      change "BK Virus" to --BHK Virus--

Page 2, 2nd Column, line 33,
      1st line of the 10th entry,      change "190 Yan et al.," to --Yan et al.,--

Page 2, 2nd Column, line 34,
      2nd line of the 10th entry,      change "(1-   )" to --(1-.)--

Page 2, 2nd Column, line 54
      1st line of the 19th entry,      change "Dr. Uytdehaag" to --Dr. UytdeHaag--

Signed and Sealed this
Twenty-ninth Day of March, 2011

David J. Kappos
*Director of the United States Patent and Trademark Office*

CERTIFICATE OF CORRECTION (continued)
U.S. Pat. No. 7,521,220 B2

On the title page:
In ITEM (56) References Cited
OTHER PUBLICATIONS (continued)
Page 2, 2nd Column, line 68,
1st line of the 24th entry,    change "#Boutl et al.," to --#Bout et al.,--

Page 3, 2nd Column, line 15,
2nd line of the 5th entry,    change "antibioties," to --antibodies,--

In the specification:

| | | |
|---|---|---|
| COLUMN 4, | LINE 65, | change "containing virus" to --containing the virus-- |
| COLUMN 5, | LINE 7, | change "infection (mois)" to --infections (mois)-- |
| COLUMN 6, | LINE 15, | change "Spearnan-Karber" to --Spearman-Karber-- |
| COLUMN 6, | LINE 23, | change "PER.C6 cells" to --PER.C6 cell-- |
| COLUMN 6, | LINE 30, | change "PER.C6 in" to --PER.C6 cells in-- |
| COLUMN 7, | LINE 44, | change "decreasing amount" to --decreasing amounts-- |
| COLUMN 10, | LINE 57, | change "500 KD." to --500 kD.-- |
| COLUMN 10, | LINE 58, | change "750 KD." to --750 kD.-- |
| COLUMN 10, | LINE 61, | change "500 KD" to --500 kD-- |
| COLUMN 10, | LINE 62, | change "KD." to --kD.-- |
| COLUMN 13, | LINE 31, | change "infection (mois)" to --infections (mois)-- |
| COLUMN 15, | LINE 51, | change "alpha 2-6" to --alpha2-6-- |
| COLUMN 22, | LINE 55, | change "moi 1" to --moi of 1-- |
| COLUMN 24, | LINE 53, | change "with moi" to --with mois-- |
| COLUMN 26, | LINE 25, | change "TCID50." to --TCID$_{50}$.-- |
| COLUMN 26, | LINE 26, | change "TCID50" to --TCID$_{50}$-- |
| COLUMN 26, | LINE 38, | change "TCID50" to --TCID$_{50}$-- |
| COLUMN 28, | LINE 67, | change "179:35-40" to --179:35-40.-- |
| COLUMN 30, | LINE 9, | change "196:660665." to --196:660-665.-- |

In the claims:
CLAIM 14, COLUMN 34, LINE 16,    change "14. The process of claim 1," to
--14. The method of claim 1,--